(12) United States Patent
Yang et al.

(10) Patent No.: US 12,076,334 B2
(45) Date of Patent: Sep. 3, 2024

(54) PHARMACEUTICAL COMPOSITION COMPRISING ADENOSINE DERIVATIVE FOR PREVENTION AND TREATMENT OF RETINAL DISEASE OR OPTIC NERVE DISEASE

(71) Applicant: FUTURE MEDICINE CO., LTD., Seoul (KR)

(72) Inventors: Jae Wook Yang, Busan (KR); Jee Young Kim, Busan (KR); Hyuk Woo Lee, Hwaseong-si (KR); Chong-Woo Park, Seoul (KR); Mi Ra Yu, Seoul (KR); Ji Youn Lee, Suwon-si (KR); Bo Mi Park, Yongin-si (KR)

(73) Assignee: FUTURE MEDICINE CO., LTD., Seoul (KR)

( * ) Notice: Subject to any disclaimer, the term of this patent is extended or adjusted under 35 U.S.C. 154(b) by 0 days.

(21) Appl. No.: 17/866,990

(22) Filed: Jul. 18, 2022

(65) Prior Publication Data

US 2023/0095356 A1 Mar. 30, 2023

Related U.S. Application Data

(62) Division of application No. 16/767,489, filed as application No. PCT/KR2018/014943 on Nov. 29, 2018, now abandoned.

(30) Foreign Application Priority Data

Nov. 29, 2017 (KR) ........................ 10-2017-0161545

(51) Int. Cl.
| | | |
|---|---|---|
| *A61K 31/7076* | (2006.01) | |
| *A61K 9/00* | (2006.01) | |
| *A61K 47/38* | (2006.01) | |
| *A61P 27/02* | (2006.01) | |

(52) U.S. Cl.
CPC ........ *A61K 31/7076* (2013.01); *A61K 9/0048* (2013.01); *A61K 47/38* (2013.01); *A61P 27/02* (2018.01)

(58) Field of Classification Search
CPC ...... A61K 31/7076; A61K 47/38; A61P 27/02
See application file for complete search history.

(56) References Cited

U.S. PATENT DOCUMENTS

| 2004/0053982 A1 | 3/2004 | Press et al. |
| 2012/0252823 A1 | 10/2012 | Jacobson et al. |
| 2014/0275128 A1 | 9/2014 | McVicar |

FOREIGN PATENT DOCUMENTS

| EP | 3 603 647 A1 | 2/2020 |
| JP | 3881174 B2 | 11/2006 |
| KR | 10-2009-0128495 A | 12/2009 |
| KR | 10-1396092 B1 | 5/2014 |
| KR | 10-1709307 B1 | 2/2017 |
| KR | 10-1805400 B1 | 12/2017 |
| WO | 2008/045330 A2 | 4/2008 |
| WO | 2012/125400 A1 | 9/2012 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Zhang et al., Nature Reviews Drug Discovery, 2012, 11, p. 541-559. (Year: 2012).*
Von Troostenburg et al., International Journal of Clinical Pharmacology and Therapeutics, 2004, 42(10), p. 534-542. (Year: 2004).*
Galvao et al., Experimental Eye Research, 2015, 140, p. 65-74. (Year: 2015).*
International Search Report issued by the Korean Intellectual Property Office for corresponding International Patent Application No. PCT/KR2018/014943, mailed on Mar. 13, 2019, with an English translation.
Jacobson et al., "Adenosine Receptors: Pharmacology, Structure-Activity Relationships, and Therapeutic Potential" J. Med. Chem. vol. 35, Feb. 7, 1992, pp. 407-422.
Zhou et al., "Molecular cloning and characterization of an adenosine receptor: The A3 adenosine receptor" Proc. Natl. Acad. Sci., USA, vol. 89, Aug. 1992, pp. 7432-7436.
Ramkumar et al., "The A3 Adenosine Receptor Is the Unique Adenosine Receptor Which Facilitates Release of Allergic Mediators in Mast Cells", Journal of Biological Chemistry vol. 268, 1993, pp. 16887-16890.
Abbracchio et al., "G Protein-Dependent Activation of Phospholipase C by Adenosine A3 Receptors in Rat Brain", Molecular Pharmacology vol. 48, 1995, pp. 1038-1045.
Baraldi et al., "Pyrazolo[4,3-e]1,2,4-Triazolo[1,5-c]Pyrimidine Ligands, New Tools to Characterize A3 Adenosine Receptors in Human Tumor Cell Lines", Current Medical Chemistry vol. 12, 2005, pp. 1319-1329.
Böhm et al., "The pro-inflammatory role of high-mobility group box 1 protein (HMGB-1) in photoreceptors and retinal explants exposed to elevated pressure", Laboratory Investigation (2016) vol. 96, 2016, pp. 409-427.
Wang et al., "Nucleoside-Derived Antagonists to A3 Adenosine Receptors Lower Mouse Intraocular Pressure and Act across Species", Experimental Eye Research, 2010, vol. 90, No. 1, pp. 146-154.
Non-Final Office Action issued by the United States Patent and Trademark Office for corresponding U.S. Appl. No. 16/767,489, electronically delivered on Dec. 21, 2021.
Jacobson et al., "A3 Adenosine Receptors as Modulators of Inflammation: From Medicinal Chemistry to Therapy", Med Res Rev, Jul. 2018, pp. 1-60, 38(4): 1031-1072, doi: 10.1002/med 21456: HHS Public Access, USA.
Gennaro A. R., ed., Remington's Pharmaceutical Sciences, 17th edition, 1985, pp. 1406-1677.

* cited by examiner

*Primary Examiner* — Jonathan S Lau
(74) *Attorney, Agent, or Firm* — Myers Wolin, LLC

(57) ABSTRACT

The present disclosure relates to a pharmaceutical composition, an oral administration agent and an eye drop for preventing or treating retinal diseases or optic nerve diseases including the compound represented by the Chemical Formula 1 or a pharmaceutically acceptable salt thereof as an active ingredient and the pharmaceutical composition, the oral administration agent and the eye drop can effectively prevent or treat retinal disease or optic nerve disease.

8 Claims, 14 Drawing Sheets

Specification includes a Sequence Listing.

PHARMACEUTICAL COMPOSITION COMPRISING ADENOSINE DERIVATIVE FOR PREVENTION AND TREATMENT OF RETINAL DISEASE OR OPTIC NERVE DISEASE

CROSS-REFERENCE TO RELATED APPLICATION

This application is a divisional application of U.S. application Ser. No. 16/767,489 filed on May 27, 2020, now pending, which is a national stage application of International Application PCT/KR2018/014943, filed on Nov. 29, 2018 and designated the U.S., which claims priority to Korean Patent Application No. 10-2017-0161545, filed on Nov. 29, 2017. The contents of each are herein incorporated by reference.

The contents of the Sequence Listing XML file are herein incorporated by reference. The name of the Sequence Listing XML file is "beeip_10055B_Sequence.xml." The date of creation of the Sequence Listing XML file is Sep. 22, 2022. The size of the Sequence Listing XML file in bytes is 11 kilo bytes.

TECHNICAL FIELD

The present disclosure relates to a composition for preventing or treating retinal disease or optic nerve disease comprising an adenosine derivative.

BACKGROUND ART

Adenosine is a substance that performs many physiological functions through a receptor on a special cell membrane and adenosine that exists outside the cell acts as a neurotransmitter in many physiological systems, and generally it compensates for the hyperactivity of a given organ and acts to protect against the harmful effects of stress (Jacobson, K A et al., J. Med. Chem., 35, 407-422, 1992). This action is due to a partially generated negative feedback loop, which attempts to reduce the energy demands of the cells by adenosine produced by the breakdown of intracellular or extracellular ATP (adenosine triphosphate) and increase the supply of oxygen. Adenosine is important for maintaining homeostasis of essential organs such as the brain, heart, kidneys and for example, the administration of adenosine agonists from the outside to the brain has been shown to have neuroprotective effects and it is also known to be involved in pain, cognition, exercise or sleep.

Adenosine receptors have been classified into P1 and P2 receptors, respectively, through pharmacological studies and molecular cloning to date. Adenosine acts as a substrate for the P1 receptor, and ATP, ADP, UTP and UDP act as a substrate for the P2 receptor, thereby expressing physiological activity. Among them, four different subtypes of adenosine receptors were identified as P1 receptors, which are classified as $A_1$, $A_2$ or $A_3$ according to affinity for ligands, distribution in the body, route of action and the like, and again $A_2$ is classified as $A_{2A}$ and $A_{2B}$. These adenosine receptors are a class of the G-protein-coupled receptor group, and adenosine $A_1$, $A_{2A}$ and $A_{2B}$ receptors have been pharmacologically identified using many selective ligands, but the adenosine $A_3$ receptor was first discovered in 1992 (Zhou, Q. Y, et al., Proc. Natl. Acad. Sci., USA, 89, 7432-7436, 1992) and much research has been performed to confirm the pathophysiological function of this receptor.

Adenosine $A_1$ and $A_2$ receptor agonists are mainly derivatives of adenosine, which have been actively studied as antihypertensive agents, antipsychotics, arrhythmia drugs, fat metabolism inhibitors (diabetes drugs) and brain protectors, and their antagonists are xanthine derivatives or a fused bicyclic ring, and is being developed as an asthma therapeutic agent, antidepressant, arrhythmia therapeutic agent, kidney protectant, Parkinson's disease therapeutic agent and intelligence development agent, etc. Nonetheless, what is currently commercialized is only adenosine itself, which is used for the treatment of supraventricular tachycardia, and dipyridamole, an adenosine transport inhibitor that is used as an adjuvant for warfarin to prevent blood clotting after heart surgery. The reason why such commercialization is not smooth is that because adenosine receptors are spread all over the body, it is due to various pharmacological actions accompanied by the activation of the receptors, and that is, there is no compound capable of activating only the adenosine receptors of a desired tissue.

Among the adenosine receptors, the adenosine $A_3$ receptor is the most recently discovered receptor unlike the well-known adenosine $A_1$ and $A_2$ receptors, and its role is not well known and many studies are ongoing to develop selective receptor modulators. To pharmacologically study the adenosine $A_3$ receptor, three radiolabeled ligands are used, which are [$^{125}$I]ABA($N^6$-(4-amino-3-[$^{125}$I]iodobenzyl)-adenosine, $N^6$-(4-amino-3-[$^{125}$I]iodobenzyl)-adenosine), [$^{125}$I]APNEA($N^6$-2-(4-amino-3-[$^{125}$I]iodophenyl)-ethyladenosine, $N^6$-2-(4-amino-3-[$^{125}$I]iodophenyl)-ethyladenosine) or [$^{125}$I]AB-MECA(($N^6$-(4-amino-3-[$^{125}$I]iodobenzyl)-adenosine-5'-N-methylcarboxamide, $N^6$-(4-amino-3-[$^{125}$I]iodobenzyl)-adenosine-5'-N-methylcarboxamide). Through pharmacological studies using the radiolabeled ligand, it is demonstrated that when the adenosine $A_3$ receptor is expressed in Chinese Hamster Ovary (CHO) cells, the $A_3$ receptor has an inhibitory action of adenylyl cyclase, an enzyme that produces cAMP from ATP, and when the $A_3$ receptor is activated by an agonist, GTP-dependent phospholipase (Guanosine triphosphate-dependent phospholipase C), an enzyme that breaks down phosphatidyl inositol in the brain to produce inositol phosphate and DAG, was activated (Ramkumar, V. et al., J. Biol. Chem., 268, 168871-168890, 1993; Abbracchio, M P et al., Mol Pharmacol., 48, 1038-1045, 1995). This discovery makes it possible to explain the possibility of a response pathway by $A_3$ receptor activation in brain ischemia and it is because this secondary transmitter system means a response pathway of neurological injury in brain ischemia. In addition, it is known that agonists of the $A_3$ receptor inhibit the release of tumor necrosis factor (TNF-α), an inflammatory mediator, and also suppresses the production of inflammatory mediators, MIP-1α, interleukin-12 and interferon-γ and protects the heart as well as the protective effect against brain diseases such as epilepsy. Inactivation of the adenosine $A_3$ receptor causes the release of inflammatory factors such as histamine from mast cells, acts to contract the bronchi, and also causes apoptosis in immune cells. Therefore, since adenosine $A_3$ receptor antagonists have potential for development as anti-inflammatory and asthma therapeutic agents, it is possible to develop new therapeutic drugs for various diseases such as asthma, inflammation, brain ischemia, heart disease and cancer, if compounds with pharmacological selectivity can be developed.

Among the materials that have been researched and developed to date, a representative human adenosine $A_3$ receptor agonist is nucleoside family, $N^6$-(3-iodobenzyl)-5'-(N-methylcarbamoyl)-adenosine (IB-MECA) and $N^6$-(3-iodobenzyl)-2-chloro-5'-(N-methylcarbamoyl)-adenosine (CI-IB-MECA), which is a substance having high affinity and selectivity for the $A_3$ receptor compared to the adenosine $A_1$ and $A_2$ receptors. On the other hand, disadvantage has been noted that adenosine $A_3$ receptor antagonists, which exhibit high affinity and selectivity are mostly nonpurine-based bicyclic ring compounds, not nucleoside backbones, and because they exhibit high activity in human receptors, but they have little or no activity against the $A_3$ receptor in rats, it is not possible to test animals that are essential for the development of drugs that can be clinically applied (Baraldi, P G et al., Curr. Med. Chem., 12, 1319-1329, 2005). However, compared to the nonpurine-based bicyclic ring compound, the nucleoside-based compound exhibits high affinity and selectivity regardless of species, so it is considered to have a great advantage in animal experiments, so the potential for development as a new drug is very high. Therefore, it is an urgent task to derive a selective adenosine $A_3$ receptor antagonist from this type.

On the other hand, the retina is a transparent and thin film located on the innermost part of the eye ball wall and in contact with the vitreous body in the eye ball. It converts the optical information of an object into an electrical signal and serves as the primary visual information organ that delivers images through the visual nerve to the central visual area of the brain. The retina consists of more than 100 million light-sensing cells (light-sensitive photoreceptor cells), more than 1 million visual nerve cells, ganglion cells, and numerous nerve cells that act as a wire for connecting them, and thus it is the most sophisticated tissue in our body. The *Macula lutea*, the central part of the retina that distinguishes color and objects and represents vision, consists of a light-sensitive photoreceptor cells layer composed of conical cells and a ganglion cells layer, which makes the retina thin and converts from the electrical signal of the image into chemical signal in bright light and transmits to the brain through the axon of the ganglion cells, the optic nerve, and the retina other than the *Macula lutea* recognizes the periphery and plays a major role in the dark. On the other hand, if an abnormality occurs in the retina due to aging or external factors, it gradually leads to blindness with visual impairment that causes problems with visual acuity and visual filed.

Retinal disease is occurred by abnormalities in the retina peripheral tissue and retinal detachment and it is classified into three types of retinal detachment in which the retina is detached into the back of the eye ball to cause visual impairment; peripheral retinal degeneration causing abnormalities in retina peripheral tissue; and macular degeneration causing abnormalities in the *Macula lutea*. Once the retina is separated from the pigment epithelial layer, it is unable to receive optical information regarding the image, and it is also unable to supply nutrients from the choroid and thus nerve cells cannot function and if this condition is left unattended, permanent retinal atrophy occurs, leading to blindness. The main cause of blindness is a retinal disease which is mainly caused by aging and also can be caused by genetic or excessive myopia, trauma, etc. and is the second most common ophthalmic disease after cataracts. Retinal disease is not a fatal disease that leads to death, but the onset has increased rapidly in recent years due to industrialization and dietary changes along with the increase in the elderly population and thus it is necessary to develop a composition for the treatment of retinal diseases that can be supplied in the form of crude drugs that have been conventionally ingested and are not a therapeutic agent synthesized artificially besides the surgical method.

DISCLOSURE

Technical Problem

An object of the present disclosure is to provide a pharmaceutical composition, an oral administration agent or eye drops which can effectively prevent or treat retinal diseases.

Another object of the present disclosure is to provide a pharmaceutical composition, an oral administration agent or eye drops which can effectively prevent or treat optic nerve diseases.

Technical Solution

In order to achieve the above object, the present disclosure provides a pharmaceutical composition for preventing or treating retinal disease comprising a compound represented by the following Chemical Formula 1 or a pharmaceutically acceptable salt thereof as an active ingredient.

Also, the present disclosure provides an oral administration agent for preventing or treating retinal disease comprising a compound represented by the following Chemical Formula 1 or a pharmaceutically acceptable salt thereof as an active ingredient.

In addition, the present disclosure provides an eye drop for preventing or treating retinal disease comprising a compound represented by the following Chemical Formula 1 or a pharmaceutically acceptable salt thereof as an active ingredient.

In order to achieve the above other object, the present disclosure provides a pharmaceutical composition for preventing or treating optic nerve disease comprising a compound represented by the following Chemical Formula 1 or a pharmaceutically acceptable salt thereof as an active ingredient.

Also, the present disclosure provides an oral administration agent for preventing or treating optic nerve disease comprising a compound represented by the following Chemical Formula 1 or a pharmaceutically acceptable salt thereof as an active ingredient.

In addition, the present disclosure provides an eye drop for preventing or treating optic nerve disease comprising a compound represented by the following Chemical Formula 1 or a pharmaceutically acceptable salt thereof as an active ingredient:

[Chemical Formula 1]

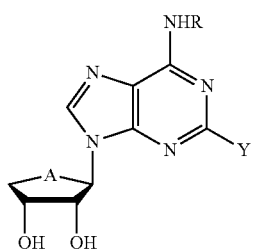

in Chemical Formula 1, A is O or S;

R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy or c) benzyl substituted with hydroxycarbonyl; and Y is H or a halogen element.

Advantageous Effects

The present disclosure relates to a composition for preventing or treating retinal disease or optic nerve disease comprising a specific adenosine derivative as an active ingredient. The adenosine derivative can suppress the inflammatory response by inhibiting the expression of inflammation-related proteins, VEGF and inflammatory cytokines in photoreceptor cells derived from the mouse retina, and can inhibit apoptosis induced by glutamic acid, and eye drops prepared by comprising the same have shown an effect of effectively protecting retinal ganglion cells in experiments with mice. Therefore, the present disclosure can effectively prevent or treat retinal disease or optic nerve disease.

DESCRIPTION OF DRAWINGS

FIG. 10A, (a) protein expression change, (b) RIP protein expression change, (c) RIP3 protein expression change; FIG. 10B, (d) pBcl2 protein expression change; (e) Bcl2 protein expression change; (f) pBad protein expression change; (g) Bad protein expression change; FIG. 10C, (h) BID protein expression changes; (i) caspase 8 protein expression changes; (j) cleaved caspase 9 protein expression changes; and (k) cleaved caspase 3 protein expression changes).

BEST MODE

Figure 1A:
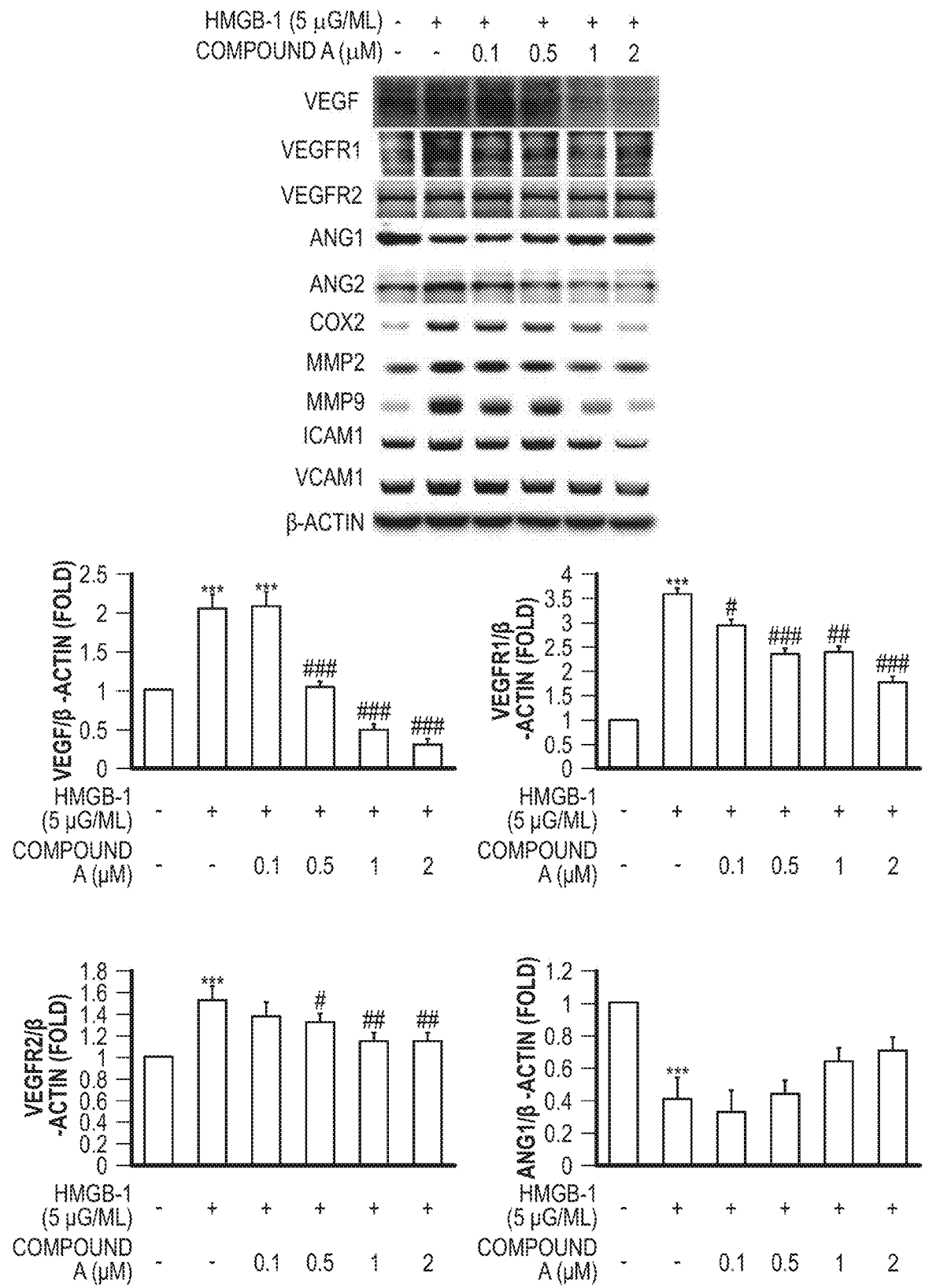
FIGS. 1A and 1B show a result of confirming a change in the protein expression related to angiogenesis and inflammatory response when Compound A is treated in an example of the present disclosure.

Hereinafter, the present disclosure will be described in more detail.

The present disclosure provides a pharmaceutical composition for preventing or treating retinal disease comprising a compound represented by Chemical Formula 1 or a pharmaceutically acceptable salt thereof as an active ingredient:

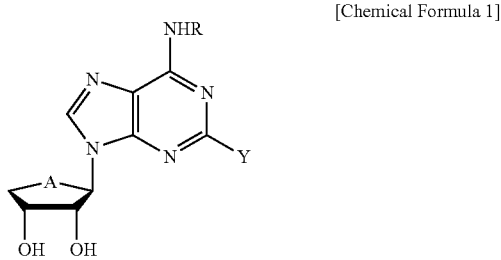

[Chemical Formula 1]

in Chemical Formula 1, A is O or S;

R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy, or c) benzyl substituted with hydroxycarbonyl; and Y is H or a halogen element.

At this time, the retinal disease may be diabetic retinopathy or age-related macular disease, but it is not limited thereto.

Preferably, in the above Chemical Formula 1, A may be O or S, R may be methyl, ethyl, propyl, naphthylmethyl, benzyl, benzyl substituted independently or optionally with 1 or 2 or more substituents selected from the group consisting of fluoro, chloro, bromo or $C_1$ to $C_3$ alkoxy or toluic acid, and Y may be H or Cl.

More preferably, A is O or S, R is methyl, ethyl, 1-naphthylmethyl, benzyl, 2-chlorobenzyl, 3-fluorobenzyl, 3-chlorobenzyl, 3-bromobenzyl, 2-methoxy-5-chlorobenzyl, 2-methoxybenzyl or 3-toluic acid, and Y is H or Cl.

Preferred examples of the adenosine derivative represented by Chemical Formula 1 according to the present disclosure are as follows:

(1) (2R,3R,4S)-2-(2-chloro-6-(3-fluorobenzylamino)-9H-purin-9-yl) tetrahydrothiophene-3,4-diol;

(2) (2R,3R,4S)-2-(2-chloro-6-(3-chlorobenzylamino)-9H-purin-9-yl) tetrahydrothiophene-3,4-diol;

(3) (2R,3R,4S)-2-(6-(3-bromobenzylamino)-2-chloro-9H-purin-9-yl) tetrahydrothiophene-3,4-diol;

(4) (2R,3R,4S)-2-(2-chloro-6-(2-chlorobenzylamino)-9H-purin-9-yl) tetrahydrothiophene-3,4-diol;

(5) (2R,3R,4S)-2-(2-chloro-6-(5-chloro-2-methoxybenzylamino)-9H-purin-9-yl)tetrahydrothiophene-3,4-diol;

(6) (2R,3R,4S)-2-(2-chloro-6-(2-methoxybenzylamino)-9H-purin-9-yl)tetrahydrothiophene-3,4-diol;
(7) (2R,3R,4S)-2-(2-chloro-6-(naphthalen-1-ylmethyl-amino)-9H-purin-9-yl)tetrahydrothiophene-3,4-diol;
(8) 3-((2-chloro-9-((2R,3R,4S)-3,4-dihydroxytetrahydrothiophen-2-yl)-9H-purin-6-ylamino)methyl)benzoic acid;
(9) 2-(2-chloro-6-methylamino-purin-9-yl)tetrahydrothiophene-3,4-diol;
(10) (2R,3R,4S)-2-(6-(3-fluorobenzylamino)-9H-purin-9-yl)tetrahydrothiophene-3,4-diol;
(11) (2R,3R,4S)-2-(6-(3-chlorobenzylamino)-9H-purin-9-yl)tetrahydrothiophene-3,4-diol;
(12) (2R,3R,4S)-2-(6-(3-bromobenzylamino)-9H-purin-9-yl)tetrahydrothiophene-3,4-diol; and
(13) (2R,3R,4R)-2-(6-(3-bromobenzylamino)-2-chloro-9H-purin-9-yl)tetrahydrofuran-3,4-diol.

Most preferably, the compound represented by Chemical Formula 1 may be a compound represented by Chemical Formula 2:

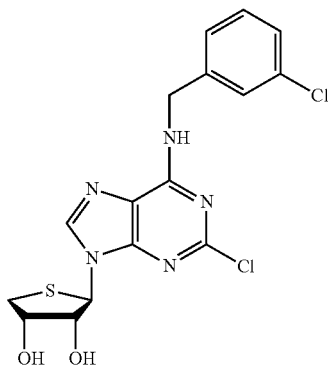

[Chemical Formula 2]

In addition, the present disclosure provides an oral administration agent for preventing or treating retinal disease comprising a compound represented by Chemical Formula 1 or a pharmaceutically acceptable salt thereof as an active ingredient:

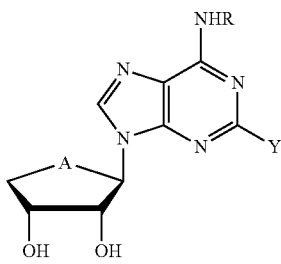

[Chemical Formula 1]

in Chemical Formula 1, A is O or S;
R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy, or c) benzyl substituted with hydroxycarbonyl; and Y is H or a halogen element.

At this time, the retinal disease may be diabetic retinopathy or age-related macular disease, but it is not limited thereto.

Preferably, in the above Chemical Formula 1, A may be O or S, R may be methyl, ethyl, propyl, naphthylmethyl, benzyl, benzyl substituted independently or optionally with 1 or 2 or more substituents selected from the group consisting of fluoro, chloro, bromo or $C_1$ to $C_3$ alkoxy or toluic acid, and Y may be H or Cl.

More preferably, A is O or S, R is methyl, ethyl, 1-naphthylmethyl, benzyl, 2-chlorobenzyl, 3-fluorobenzyl, 3-chlorobenzyl, 3-bromobenzyl, 2-methoxy-5-chlorobenzyl, 2-methoxybenzyl or 3-toluic acid, and Y is H or Cl.

Most preferably, the compound represented by Chemical Formula 1 may be a compound represented by Chemical Formula 2:

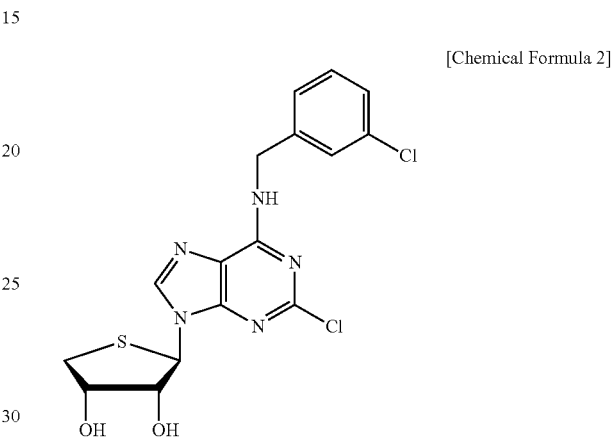

[Chemical Formula 2]

Furthermore, the present disclosure provides An eye drop for preventing or treating retinal disease comprising a compound represented by Chemical Formula 1 or a pharmaceutically acceptable salt thereof as an active ingredient:

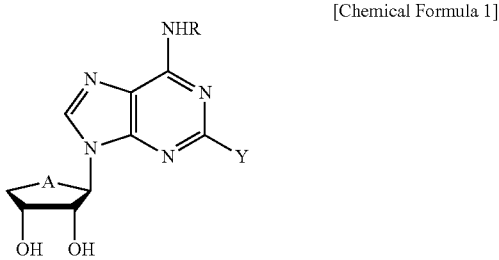

[Chemical Formula 1]

in Chemical Formula 1, A is O or S;
R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy, or c) benzyl substituted with hydroxycarbonyl; and Y is H or a halogen element.

In this case, the retinal disease may be diabetic retinopathy or age-related macular disease, but it is not limited thereto.

Preferably, in the above Chemical Formula 1, A may be O or S, R may be methyl, ethyl, propyl, naphthylmethyl, benzyl, benzyl substituted independently or optionally with 1 or 2 or more substituents selected from the group consisting of fluoro, chloro, bromo or $C_1$ to $C_3$ alkoxy or toluic acid, and Y may be H or Cl.

More preferably, A is O or S, R is methyl, ethyl, 1-naphthylmethyl, benzyl, 2-chlorobenzyl, 3-fluorobenzyl, 3-chlorobenzyl, 3-bromobenzyl, 2-methoxy-5-chlorobenzyl, 2-methoxybenzyl or 3-toluic acid, and Y is H or Cl.

Most preferably, the compound represented by the Chemical Formula 1 may be a compound represented by Chemical Formula 2:

[Chemical Formula 2]

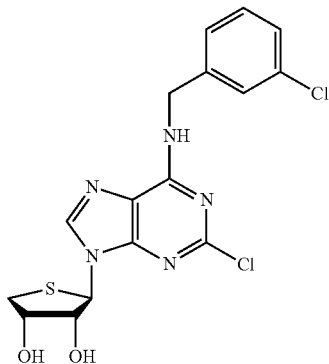

The present disclosure provides a pharmaceutical composition for preventing or treating optic nerve disease comprising a compound represented by Chemical Formula 1 or a pharmaceutically acceptable salt thereof as an active ingredient:

[Chemical Formula 1]

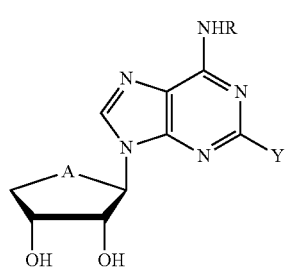

in Chemical Formula 1, A is O or S;

R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy, or c) benzyl substituted with hydroxycarbonyl; and Y is H or a halogen element.

At this time, the retinal disease may be diabetic retinopathy or age-related macular disease, but it is not limited thereto.

Preferably, in the above Chemical Formula 1, A may be O or S, R may be methyl, ethyl, propyl, naphthylmethyl, benzyl, benzyl substituted independently or optionally with 1 or 2 or more substituents selected from the group consisting of fluoro, chloro, bromo or $C_1$ to $C_3$ alkoxy or toluic acid, and Y may be H or Cl.

More preferably, A is O or S, R is methyl, ethyl, 1-naphthylmethyl, benzyl, 2-chlorobenzyl, 3-fluorobenzyl, 3-chlorobenzyl, 3-bromobenzyl, 2-methoxy-5-chlorobenzyl, 2-methoxybenzyl or 3-toluic acid, and Y is H or Cl.

Most preferably, the compound represented by the Chemical Formula 1 may be a compound represented by Chemical Formula 2:

[Chemical Formula 2]

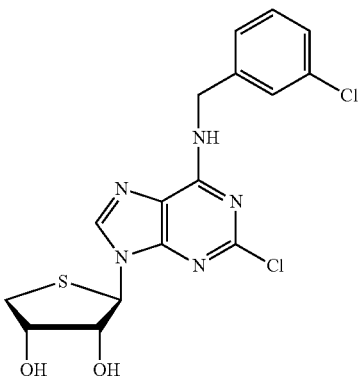

The adenosine derivative represented by the above Chemical Formula 1 according to the present disclosure can be used in the form of a pharmaceutically acceptable salt. As the salt, acid addition salts formed by various pharmaceutically acceptable organic or inorganic acids are useful. Suitable organic acids include, for example, carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methylsulfuric acid, ethylsulfuric acid, dodecylsulfuric acid, etc. Suitable inorganic acids include, for example, halogen acids such as hydrochloric acid and sulfuric acid or phosphoric acid and the like.

The adenosine derivative represented by the above Chemical Formula 1 according to the present disclosure may include all salts, hydrates and solvates that can be prepared by conventional methods, as well as pharmaceutically acceptable salts.

In addition, the pharmaceutical composition for preventing or treating retinal disease or optic nerve disease according to the present disclosure may include a pharmaceutically acceptable carrier, excipient or diluent in addition to the above-mentioned active ingredients for administration. The carrier, excipients and diluents include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil.

The pharmaceutical composition of the present disclosure can be formulated and used in the form of oral formulations such as powders, granules, tablets, capsules, suspensions, emulsions, syrups, aerosols, etc., external preparations, suppositories or sterile injectable solutions according to a conventional method. In detail, when formulated, it may be prepared using diluents or excipients such as fillers, weighting agents, binders, wetting agents, disintegrating agents, surfactants, etc., which are commonly used. Solid formulations for oral administration include tablets, pills, powders, granules, capsules, etc., but it is not limited thereto. Such a solid preparation may be prepared by mixing at least one excipient such as starch, calcium carbonate, sucrose, lactose, gelatin and the like in addition to a compound represented by the above Chemical Formula 1 or a pharmaceutically acceptable salt thereof. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin. Formulations for parenteral administration include sterile aqueous solutions, non-aqueous solutions, suspensions, emulsions, freeze-dried preparations and suppositories. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

The suitable dosage of the composition of the present disclosure depends on the patient's condition and body weight, the degree of disease, drug form and time, but it can be appropriately selected by those skilled in the art.

In addition, the present disclosure provides an oral administration agent for preventing or treating optic nerve disease comprising a compound represented by Chemical Formula 1 or a pharmaceutically acceptable salt thereof as an active ingredient:

[Chemical Formula 1]

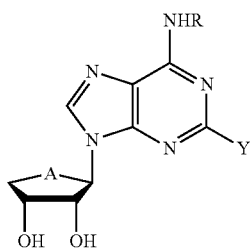

in Chemical Formula 1, A is O or S;

R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy, or c) benzyl substituted with hydroxycarbonyl; and Y is H or a halogen element.

In this case, the optic nerve disease may be selected from the group consisting of ischemic optic neuropathy, traumatic optic neuropathy and compressive optic neuropathy, but it is not limited thereto.

Preferably, in the above Chemical Formula 1, A may be O or S, R may be methyl, ethyl, propyl, naphthylmethyl, benzyl, benzyl substituted independently or optionally with 1 or 2 or more substituents selected from the group consisting of fluoro, chloro, bromo or $C_1$ to $C_3$ alkoxy or toluic acid, and Y may be H or Cl.

More preferably, A is O or S, R is methyl, ethyl, 1-naphthylmethyl, benzyl, 2-chlorobenzyl, 3-fluorobenzyl, 3-chlorobenzyl, 3-bromobenzyl, 2-methoxy-5-chlorobenzyl, 2-methoxybenzyl or 3-toluic acid, and Y is H or Cl.

Most preferably, the compound represented by the Chemical Formula 1 may be a compound represented by Chemical Formula 2:

[Chemical Formula 2]

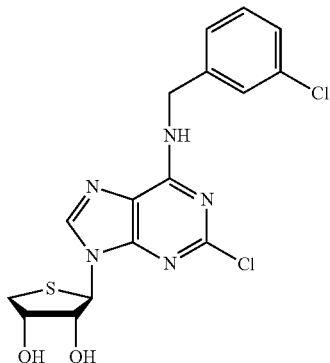

The oral administration agent for preventing or treating retinal disease or optic nerve disease may be formulated as a solid preparation or a liquid preparation of a compound represented by the above Chemical Formula 1 and/or a pharmaceutically acceptable salt thereof.

The solid preparation may be tablets, pills, powders, granules, capsules, etc. and the liquid preparation may be suspensions, solutions, emulsions, syrups, etc., but they are not limited thereto.

The oral administration agent for preventing or treating retinal disease or optic nerve disease may further include an excipient, that is at least one selected from the group consisting of methyl cellulose (MC), sucrose, lactose, dimethyl sulfoxide (DMSO), polyethylene glycol (PEG), magnesium stearate, calcium carbonate, gelatin, talc, distilled water (DW), liquid paraffin, etc., preferably at least one selected from the group consisting of methyl cellulose (MC), dimethyl sulfoxide (DMSO), polyethylene glycol (PEG) and distilled water, and more preferably, 0.5 wt % of methyl cellulose.

In the oral administration agent for preventing or treating the retinal disease or optic nerve disease according to an example of the present disclosure, the compound represented by the above Chemical Formula 1 or a pharmaceutically acceptable salt thereof may be filled in a capsule as a powder form or a solution form dissolved in the above-described excipient, but is not limited thereto.

In addition, the present disclosure provides an eye drop for preventing or treating optic nerve disease comprising a compound represented by Chemical Formula 1 or a pharmaceutically acceptable salt thereof as an active ingredient:

[Chemical Formula 1]

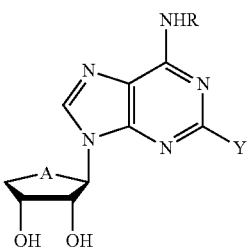

in Chemical Formula 1, A is O or S;
R is a) straight or branched $C_1$ to $C_5$ alkyl unsubstituted, or independently or optionally substituted with 1 or 2 or more $C_6$ to $C_{10}$ aryl, b) benzyl unsubstituted, or independently or optionally substituted with 1 or 2 or more fluoro, chloro, bromo or straight or branched $C_1$ to $C_4$ alkoxy, or c) benzyl substituted with hydroxycarbonyl; and Y is H or a halogen element.

In this case, the optic nerve disease may be selected from the group consisting of ischemic optic neuropathy, traumatic optic neuropathy and compressive optic neuropathy, but it is not limited thereto.

Preferably, in the above Chemical Formula 1, A may be O or S, R may be methyl, ethyl, propyl, naphthylmethyl, benzyl, benzyl substituted independently or optionally with 1 or 2 or more substituents selected from the group consisting of fluoro, chloro, bromo or $C_1$ to $C_3$ alkoxy or toluic acid, and Y may be H or Cl.

More preferably, A is O or S, R is methyl, ethyl, 1-naphthylmethyl, benzyl, 2-chlorobenzyl, 3-fluorobenzyl, 3-chlorobenzyl, 3-bromobenzyl, 2-methoxy-5-chlorobenzyl, 2-methoxybenzyl or 3-toluic acid, and Y is H or Cl.

Most preferably, the compound represented by the Chemical Formula 1 may be a compound represented by Chemical Formula 2:

[Chemical Formula 2]

The eye drop for preventing or treating retinal disease or optic nerve disease may include the compound represented by the above Chemical Formula 1 and/or a pharmaceutically acceptable salt and eye drop thereof. The eye drop may include one or more selected from the group consisting of a solubilizer, a viscosity enhancer, an antioxidant, a preservative and a buffer solution.

In one example of the present disclosure, the eye drop may be a buffer solution of pH 6.8 in which Cremophor EL, glycerin, citric acid and methylparaben are dissolved or mixed, but it is not limited thereto.

MODE FOR CARRYING OUT THE DISCLOSURE

Hereinafter, examples of the present disclosure will be described in detail to understand the present disclosure. The present disclosure may, however, be embodied in many different forms and should not be limited to the embodiments set forth herein in order to clearly illustrate the present disclosure for those skilled in the art to which the present disclosure pertains.

<Preparation Example 1> Synthesis of Adenosine Derivative Compound and Preparation of Eye Drop Adenosine derivatives were synthesized according to the method disclosed in Korean Patent No. 10-1396092. The synthesized adenosine derivative is as follows:

(2R,3R,4S)-2-(2-chloro-6-(3-fluorobenzylamino)-9H-purin-9-yl)tetrahydrothiophene-3,4-diol, (2R,3R,4S)-2-(2-chloro-6-(3-chlorobenzylamino)-9H-purin-9-yl)tetrahydrothiophene-3,4-diol, (2R,3R,4S)-2-(2-chloro-6-(3-bromobenzylamino)-9H-purin-9-yl)tetrahydrothiophene-3,4-diol, (2R,3R,4S)-2-(2-chloro-6-(2-chlorobenzylamino)-9H-purin-9-yl)tetrahydrothiophene-3,4-diol, (2R,3R,4S)-2-(2-chloro-6-(5-chloro-2-methoxybenzylamino)-9H-purin-9-yl)tetrahydrothiophene-3,4-diol, (2R,3R,4S)-2-(2-chloro-6-(2-methoxybenzylamino)-9H-purin-9-yl)tetrahydrothiophene-3,4-diol, (2R,3R,4S)-2-(2-chloro-6-(naphthalen-1-ylmethylbenzylamino)-9H-purin-9-yl)tetrahydrothiophene-3,4-diol, 3-((2-chloro-9-((2R,3S,4R)-3,4-dihydroxytetrahydrothiophen-2-yl)-9H-purin-6-ylamino)methyl)benzoic acid, 2-(2-chloro-6-methylamino-purin-9-yl)(2R,3S,4R)-tetrahydrothiophene-3,4-diol, (2R,3R,4S)-2-(6-(3-fluorobenzylamino)-9H-purin-9-yl)tetrahydrothiophene-3,4-diol, (2R,3R,4S)-2-(6-(3-chlorobenzylamino)-9H-purin-9-yl)tetrahydrothiophene-3,4-diol, (2R,3R,4S)-2-(6-(3-bromobenzylamino)-9H-purin-9-yl)tetrahydrothiophene-3,4-diol and (2R,3R,4R)-2-(6-(3-bromobenzylamino)-2-chloro-9H-purin-9-yl)tetrahydrofuran-3,4-diol.

In subsequent experiments, (2R,3R,4S)-2-(2-chloro-6-(3-chlorobenzylamino)-9H-purin-9-yl)tetrahydrothiophene-3,4-diol (hereinafter, referred to as "Compound A") was used and for animal experiments, the Compound A was mixed with a buffer solution of pH 6.8 in which cremophor EL, glycerin, citric acid and methylparaben were dissolved, and eye drops were prepared to be included at concentrations of 250 μM and 500 μM and 750 μM of the compound, respectively.

<Example 1> Confirmation of Inhibitory Effect of Adenosine Derivative Compound on Angiogenesis and Inflammatory Response 1. Experimental Method (1) Preparation and Treatment of Test Materials Compound A to be used as a test material was prepared by dissolving in DMSO. The prepared solution was stored at −20° C. until use. Treatment of the test material was treated after diluting to 1:1000 (v/v) in a serum-free cell culture medium. The control group was treated after diluting to 1:1000 (v/v) in DMSO.

(2) Analysis of Protein Expression Level in Cells when Treating Test Material

In order to confirm the efficacy of the test material in reactions related to angiogenesis and inflammatory response of photoreceptor cells derived from mouse retina, cells cultured for 24 hours under various conditions were recovered and intracellular proteins were extracted using a PRO-PREP protein extraction kit. Quantification of the extracted protein was measured using a BCA protein assay kit. 40 μg of protein was separated by 10% SDS-PAGE and then attached to the PVDF membrane. The protein-attached membrane was reacted with TBST (Tris-buffered saline with 0.1% Tween-20) containing 5% skim milk for 30 minutes and the primary antibody and secondary antibody were reacted in sequence. The protein expression level was confirmed by photographing using a Fusion Fximage acquisition system. The protein expression level was analyzed by relative values using ImageJ. Meanwhile, the antibodies and experimental conditions used for immunoblotting are summarized in Table 1 below.

TABLE 1

| Primary antibody | | | Secondary antibody | | |
|---|---|---|---|---|---|
| Antibody | Company | Dilution | Antibody | Company | Dilution |
| VEGF | Cell Signaling | 1:1,000 | Goat-anti rabbit | Santacruz | 1:5,000 |
| FLT1 (VEGFR1) | Santacruz | 1:500 | Goat-anti rabbit | Santacruz | 1:5,000 |
| FLK1 (VEGFR2) | Santacruz | 1:500 | Goat-anti rabbit | Santacruz | 1:5,000 |
| Angiopoietin1 | Santacruz | 1:500 | Rabbit-anti goat | Santacruz | 1:5,000 |
| Angiopoietin2 | Santacruz | 1:500 | Rabbit-anti goat | Santacruz | 1:5,000 |
| COX2 | Santacruz | 1:500 | Rabbit-anti goat | Santacruz | 1:5,000 |
| MMP2 | Cell Signaling | 1:1,000 | Goat-anti rabbit | Santacruz | 1:5,000 |
| MMP9 | Cell Signaling | 1:1,000 | Goat-anti rabbit | Santacruz | 1:5,000 |
| ICAM1 | Cell Signaling | 1:1,000 | Goat-anti rabbit | Santacruz | 1:5,000 |
| VCAM1 | Cell Signaling | 1:1,000 | Goat-anti rabbit | Santacruz | 1:5,000 |
| β-actin | Santacruz | 1:3,000 | Rabbit-anti mouse | Santacruz | 1:5,000 |

(3) Quantitative Analysis of Inflammatory Cytokines in Cells when Treating Test Materials In order to confirm the efficacy of the test material in reactions related to angiogenesis and inflammatory response of photoreceptor cells derived from mouse retina, cells cultured for 24 hours under various conditions were recovered and intracellular proteins were extracted using a PRO-PREP protein extraction kit. Quantification of the extracted protein was measured using a BCA protein assay kit. Quantitative analysis of inflammatory cytokines (TNFα, IL-1β, IL-6) present in the cells was analyzed with each ELISA kit.

(4) Quantitative Analysis of VEGF in Medium when Treating Test Materials

In order to confirm the efficacy of the test material in reactions related to angiogenesis of photoreceptor cells derived from mouse retina, the medium of cells cultured for 24 hours under various conditions was collected after centrifugation. Quantitative analysis of VEGF present in the medium was analyzed with the Mouse VEGF Quantikine ELISA Kit.

(5) Analysis of mRNA Expression Level in Cells when Treating Test Materials

In order to confirm the efficacy of the test material in reactions related to angiogenesis and inflammatory response of photoreceptor cells derived from mouse retina, cells cultured for 6 hours under various conditions were treated with TRIzol solution to isolate total RNA in cells. After the cDNA was synthesized using specific primers for the target gene (Table 2) and reverse transcriptase in the isolated total RNA, expression of the related factors was confirmed. mRNA expression levels were analyzed by expressing as relative values using ImageJ software.

At this time, primers and experimental conditions used for PCR analysis are summarized in Table 2 below.

TABLE 2

| Gene | Gene ID | Primer | Annealing Temp. | Cycle | Length |
|---|---|---|---|---|---|
| MMP2 | NM_008610.3 | GCTGCGCTTTTCTCGAATCC GTAAACAAGGCTTCATGGGGG | 60° C. | 30 | 375 |
| MMP9 | NM_013599.4 | CGCTCATGTACCCGCTGTAT TGTCTGCCGGACTCAAAGAC | 65° C. | 30 | 345 |
| VEGF | NM_001025250.3 | CTCCGTAGTAGCCGTGGTCT GCTTCGCTGGTAGACATCCA | 65° C. | 30 | 496 |
| FLT1 (VEGFR1) | NM_010228.3 | TCTAGAAGACTCGGGCACCT CGTGATCAGCTCCAGGTTTG | 65° C. | 30 | 403 |
| FLK1 (VEGFR2) | X70842.1 | AACACGTGGACTCTGTCCTCC GAAGAGCACGCAAACCTTCC | 65° C. | 30 | 323 |
| TNFα | NM_013693.3 | GACAAGCCTGTAGCCCACG TGGGGGCTGGGTAGAGAATG | 60° C. | 30 | 482 |
| IL-6 | NM_031168.2 | GCCTTCTTGGGACTGATGCT TGGAAATTGGGGTAGGAAGGAC | 65° C. | 30 | 475 |
| COX2 | N/A | GTATCAGAACCGCATTGCCTC CGGCTTCCAGTATTGAGGAGAACAGAT | 60° C. | 30 | 526 |
| ICAM1 | N/A | CCTGTTTCCTGCCTCTGAAG GTCTGCTGAGACCCCTCTTG | 60° C. | 30 | 528 |
| VCAM1 | N/A | TCTAGAAGACTCGGGCACCT CGTGATCAGCTCCAGGTTTG | 60° C. | 30 | 403 |
| GAPDH | NM_001289726.1 | GTGCCGTTGAATTTGCCGTGA ATGGTGAAGGTCGGTGTGAAC | 60° C. | 30 | 325 |

(6) Statistical Analysis

Measured values of each experimental group were analyzed statistically through Microsoft's Excel (2007). The outliers of the result values of each experimental group were determined by obtaining the quartiles, and the analysis of variance by one-way design of experiment of each data was performed and the results were expressed as the mean and standard deviation. In addition, the effectiveness was analyzed at a significance level of 0.05 or less through F-test and t-test (equal variance and heteroscedasticity).

2. Experimental Results (1) Changes in Expression of Proteins Related to Angiogenesis and Inflammatory Response In relation to high mobility group box 1 (HMGB-1), it has been reported that the expression of HMGB-1 was increased when pressure was applied to photoreceptor cells derived from the mouse retina, and when HMGB-1 was treated to photoreceptor cells, angiogenesis-related factors and inflammatory responses increase (Bohm M R et al., Lab Invest, 96, 409-427, 2016). Accordingly, in the present disclosure, the efficacy of adenosine derivatives against angiogenic response and inflammatory response according to damage to photoreceptor cells was verified based on the above reference.

Figure 1B:
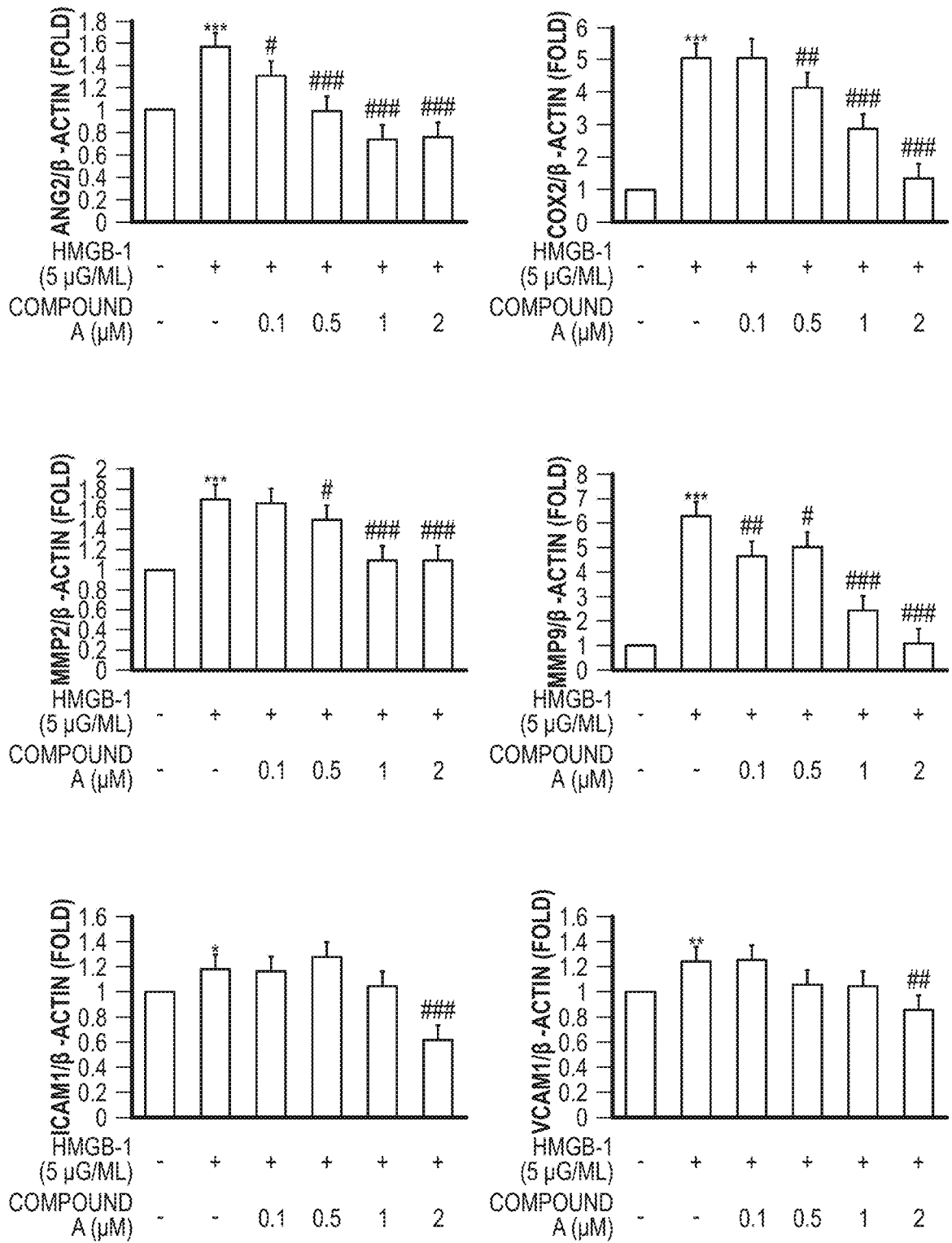

After treatment with adenosine derivatives Compound A and HMGB-1, the results of analyzing protein expression changes of angiogenic response factors such as VEGF, VEGF receptor 1, VEGF receptor 2, angiopoietin1 and angiopoietin2 enzymes and inflammatory response factors such as COX2, MMP2, MMP9, ICAM1 and VCAM1 enzymes were shown in FIG. 1A and FIG. 1B.

That is, FIG. 1A and FIG. 1B show that the expression of VEGF, VEGFR1, VEGFR2 and ANG2, which are angiogenesis-related factors, is significantly increased by HMGB-1 (5 μg/mL), and it is shown that protein expression of angiogenesis-related factors increased in a concentration-dependent manner is decreased by treatment with Compound A. The expression of VEGF and VEGFR2, COX2 and MMP2 proteins was significantly reduced at concentrations of at least 0.5 μM of Compound A and expression of VEGFR1, ANG2 and MMP9 was significantly decreased at concentrations of at least 0.1 μM. ANG1 protein expression was significantly increased at 2 μM concentration and ICAM1 and VCAM1 protein expression was significantly decreased at 2 μM concentration.

(2) Change in Expression of VEGF and Inflammatory Cytokines

Figure 2:
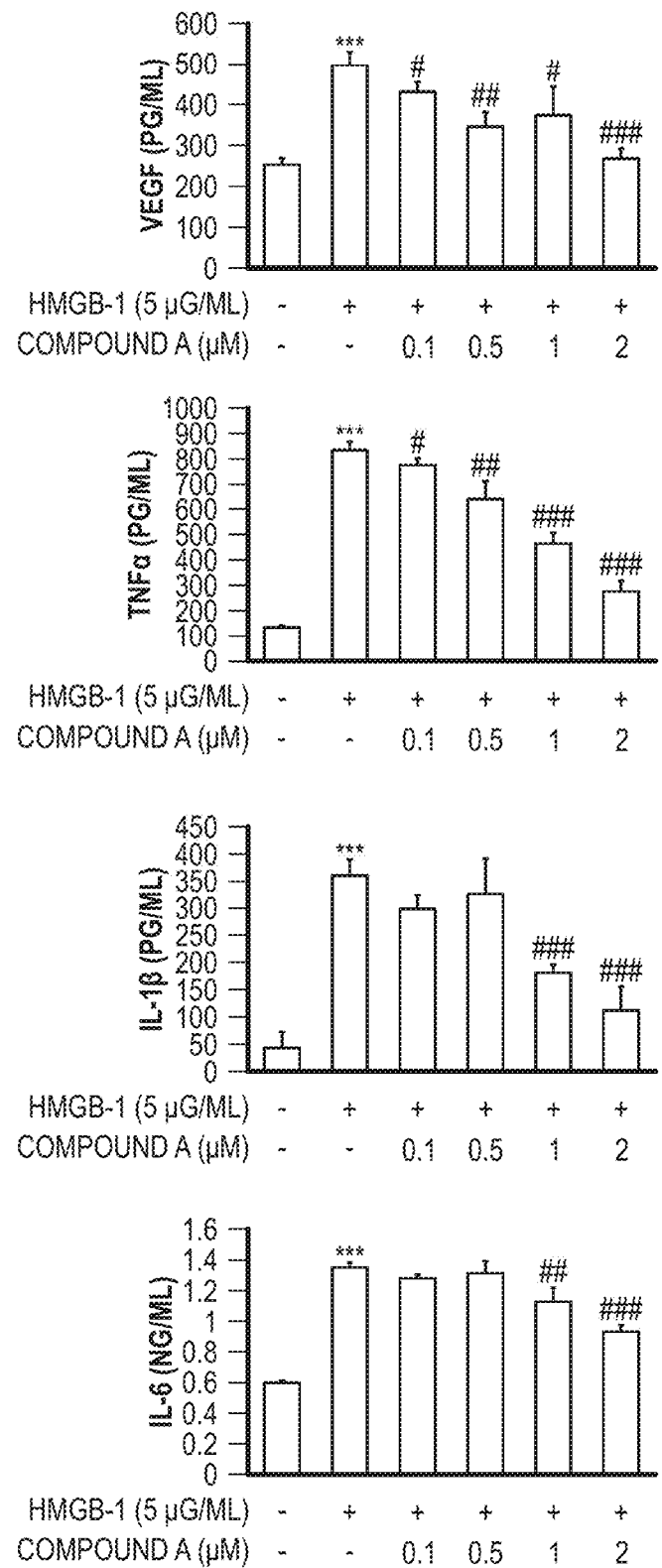
FIG. 2 shows a result of confirming a change in the expression of VEGF and inflammatory cytokines when Compound A is treated in the Example of FIGS. 1A and 1B.

As a result of performing a quantitative analysis through the ELISA analysis method to confirm the efficacy of Compound A in angiogenesis-related response and inflammatory response of mouse retinal photoreceptor cells by HMGB-1, as shown in FIG. 2, the amount of VEGF increased by HMGB-1 was significantly decreased by Compound A of 0.1 μM or more. The amount of inflammatory cytokines (TNFα, IL-1β and IL-6) in cells was increased by HMGB-1, but TNFα was significantly reduced by treatment with Compound A at concentrations of 0.1 μM or higher and IL-1β and IL-6 was significantly reduced by treatment with Compound A at concentrations of 1 μM or higher.

Figure 3A:
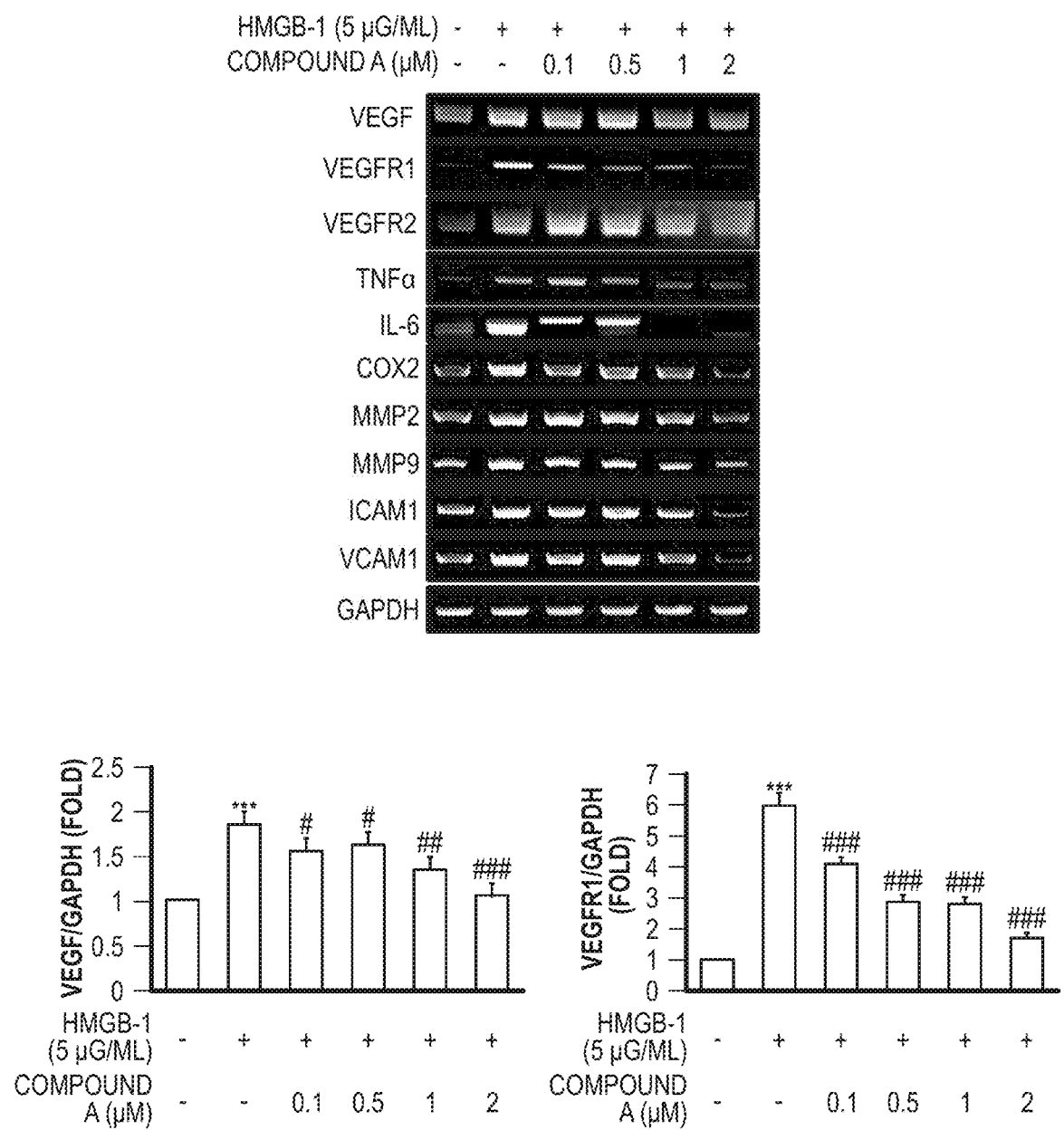
FIGS. 3A and 3B show a result of confirming a change in the expression of mRNA related to angiogenesis and inflammatory response when Compound A is treated in the Example of FIGS. 1A and 1B.
Figure 3B:
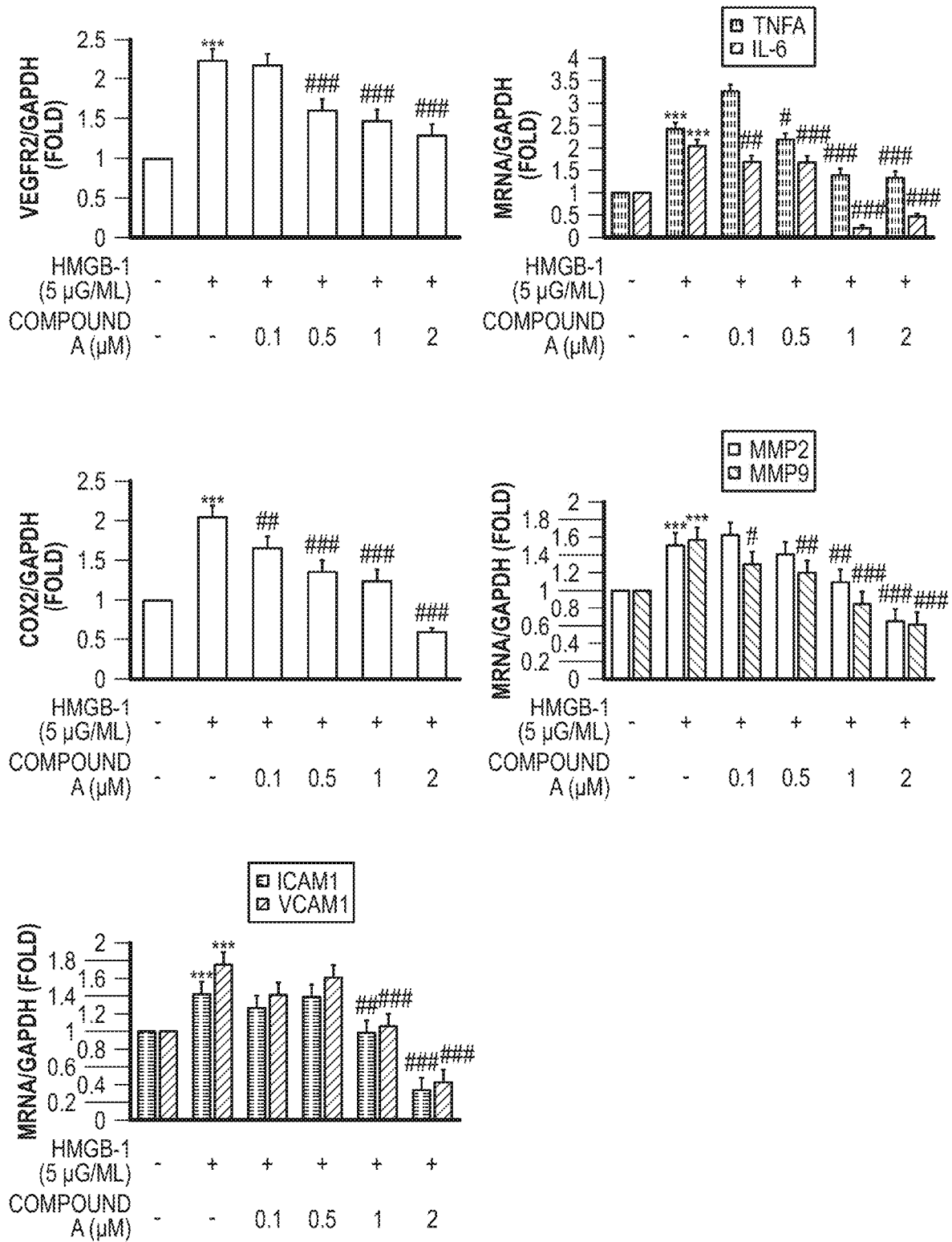

(3) Changes in mRNA Expression Related to Angiogenesis and Inflammatory Response As a result of analyzing mRNA expression changes of VEGF, VEGF receptor 1, VEGF receptor 2 enzymes, which are angiogenesis-related factors, and TNFα, IL-6, COX2, MMP2, MMP9, ICAM1 and VCAM1 enzymes, which are factors related to inflammatory response, after treatment with compound A, as shown in FIG. 3A and FIG. 3B, mRNA expression of VEGF, VEGFR1 and VEGFR2, which are angiogenesis-related factors, was significantly increased by HMGB-1. However, the mRNA expression of the angiogenesis-related factors increased by treatment with Compound A was decreased in a concentration-dependent manner. The expression of VEGF and VEGFR1 showed a significant decrease when Compound A was treated at a concentration of 0.1 μM or more, and the expression of VEGFR2 was significantly decreased at concentrations of 0.5 μM or more. In addition, the mRNA expression of TNFα, IL-6, COX2, MMP2, MMP9, ICAM1 and VCAM1, which are factors related to the inflammatory response, was also significantly increased by HMGB-1 in the control group but decreased in a concentration-dependent manner by treatment with Compound A. The expression of COX2 and IL-6 was significantly inhibited by treatment with Compound A of 0.1 μM or more and the expression of TNFα and MMP9 was significantly reduced at concentrations of 0.5 μM or more. The expression of MMP2, ICAM1 and VCAM1 was significantly reduced by treatment with Compound A at 1 μM or more.

<Example 2> Protective Effect of Adenosine Derivatives on Retinal Photoreceptor Cell 1. Experimental Method (1) Preparation and Treatment of Test Materials Compound A to be used as a test material was prepared by dissolving in DMSO. The prepared solution was stored at −20° C. until use. In addition, 10 mg of CCCP was dissolved in 1 mL of DMSO to prepare a 50 mM CCCP solution. The prepared solution was stored at −20° C. until use. Treatment of the test material was performed after diluting with a serum-free cell culture medium in 1:1000 (v/v). The control group was treated after diluting with DMSO in 1:1000 v/v).

(2) TUNEL Analysis

Quantitative analysis of apoptosis cells was analyzed by DeadEnd™ Fluorometric TUNEL System. Cells were pretreated with 1 μM of Compound A for 1 hour and then cultured for 8 hours in a medium containing 5 mM glutamic acid. Cells were washed twice with PBS and fixed with 10% formalin for 15 minutes. Fixed cells were exposed to 0.1% Triton X-100 for 10 minutes. After the cells were reacted with dUTP containing fluorescence, the cut DNA portion was stained and then fixed on a slide with a mounting solution containing DAPI. The stained cells were observed through a fluorescence microscope.

(3) Caspase 3/7 Activity Assay

The activity of intracellular caspase 3/7 was analyzed by Caspase-Glo 3/7 assay system. Cells were pretreated with 1 μM of Compound A for 1 hour and then cultured for 24 hours in a medium containing 5 mM glutamic acid. After adding the kit solution in the same amount as the cell culture medium and reacting for 1 hour, the relative activity was analyzed by measuring the amount of generated luminescence through a microplate reader.

(4) Caspase 8 Activity Assay

The activity of intracellular caspase 8 was analyzed by Caspase-Glo 8 assay system. Cells were pretreated with 1 μM of Compound A for 1 hour and then cultured for 24 hours in a medium containing 5 mM glutamic acid. After adding the kit solution in the same amount as the cell culture medium and reacting for 1 hour, the relative activity was analyzed by measuring the amount of generated luminescence through a microplate reader.

(5) Mitochondrial Cell Membrane Potential Analysis

Intracellular mitochondrial cell membrane potential was analyzed using JC-1 reagent. Cells were pretreated with 1 μM of Compound A for 1 hour and then cultured for 6 hours in a medium containing 5 mM glutamic acid. Thereafter, 5 mM of JC-1 was treated and incubated for 30 minutes. JC-1 aggregates and JC-1 monomers were analyzed by using an Attune Acoustic Focusing Cytometer at excitation wavelengths of 485±11 nm and 535±17.5 nm and emission wavelengths of 530±15 and 590±17.5 nm.

(6) Intercellular Protein Expression Level Analysis

In order to confirm the efficacy of a test material for angiogenesis-related response and inflammatory response of a mouse retina-derived photoreceptor cell, cells cultured for 24 hours under various conditions were collected and intracellular protein was extracted by using a PRO-PREP protein extraction kit. Quantification of the extracted protein was measured using a BCA protein assay kit. 40 μg of protein was separated by 10% SDS-PAGE and then attached to a PVDF membrane. The protein-attached membrane was reacted with Tris-buffered saline with 0.1% Tween-20 (TBST) containing 5% skim milk for 30 minutes, followed by reactions of primary and secondary antibodies in sequence. The protein expression level was confirmed using photograph by a Fusion Fximage acquisition system. The protein expression level was analyzed by expressing as a relative value using ImageJ. Meanwhile, the antibodies and experimental conditions used in the immunoblot analysis are summarized in Table 3 below.

TABLE 3

| Primaly antibody | | |
|---|---|---|
| Antibody | Company | Dilution |
| Mouse anti-AIF | Santacruz | 1:1,000 |
| Mouse anti-cytochrome c | Santacruz | 1:1,000 |
| Mouse anti-LaminB | Santacruz | 1:1,000 |
| Mouse anti-COX IV | Santacruz | 1:1,000 |
| Mouse anti-β-actin | Santactuz | 1:3,000 |
| Mouse anti-GAPDH | Santacruz | 1:3,000 |
| Mouse anti-Bcl$_2$ | Santacruz | 1:500 |
| Mouse anti-pBcl$_2$ | Santacruz | 1:500 |
| Mouse anti-BID | Santacruz | 1:200 |
| Rabbit anti-BAD | Cell signaling | 1:1,000 |
| Rabbit anti-pBAD | Cell signaling | 1:1,000 |
| Rabbit anti-cleaved caspase 3 | Cell signaling | 1:1,000 |
| Mouse anti-caspase 8 | Cell signaling | 1:1,000 |
| Rabbit anti-cleaved caspase 9 | Cell signaling | 1:1,000 |
| Rabbit anti-RIP | Santacruz | 1:500 |
| Mouse anti-RIP3 | Santacruz | 1:500 |

(7) Statistical Analysis

The measured value of each experimental group was statistically analyzed through SPSS 23.0 of IBM. When the equal variance of each experimental group was one variance, the analysis was performed by one-way analysis of variance and Tukeys test and in the case of heteroscedasticity, it was performed by one-way analysis of variance and Welchs t-test. The experimental group showing significant statistical difference from the normal group was shown as *P<0.05, *P<0.01, ***P<0.001, and the experimental group showing significant statistical difference from the control group treated with only glutamate was shown as #P<0.05, ##P<0.01, ###P<0.001.

2. Experimental Results (1) Cytotoxicity of Glutamic Acid

Figure 4:
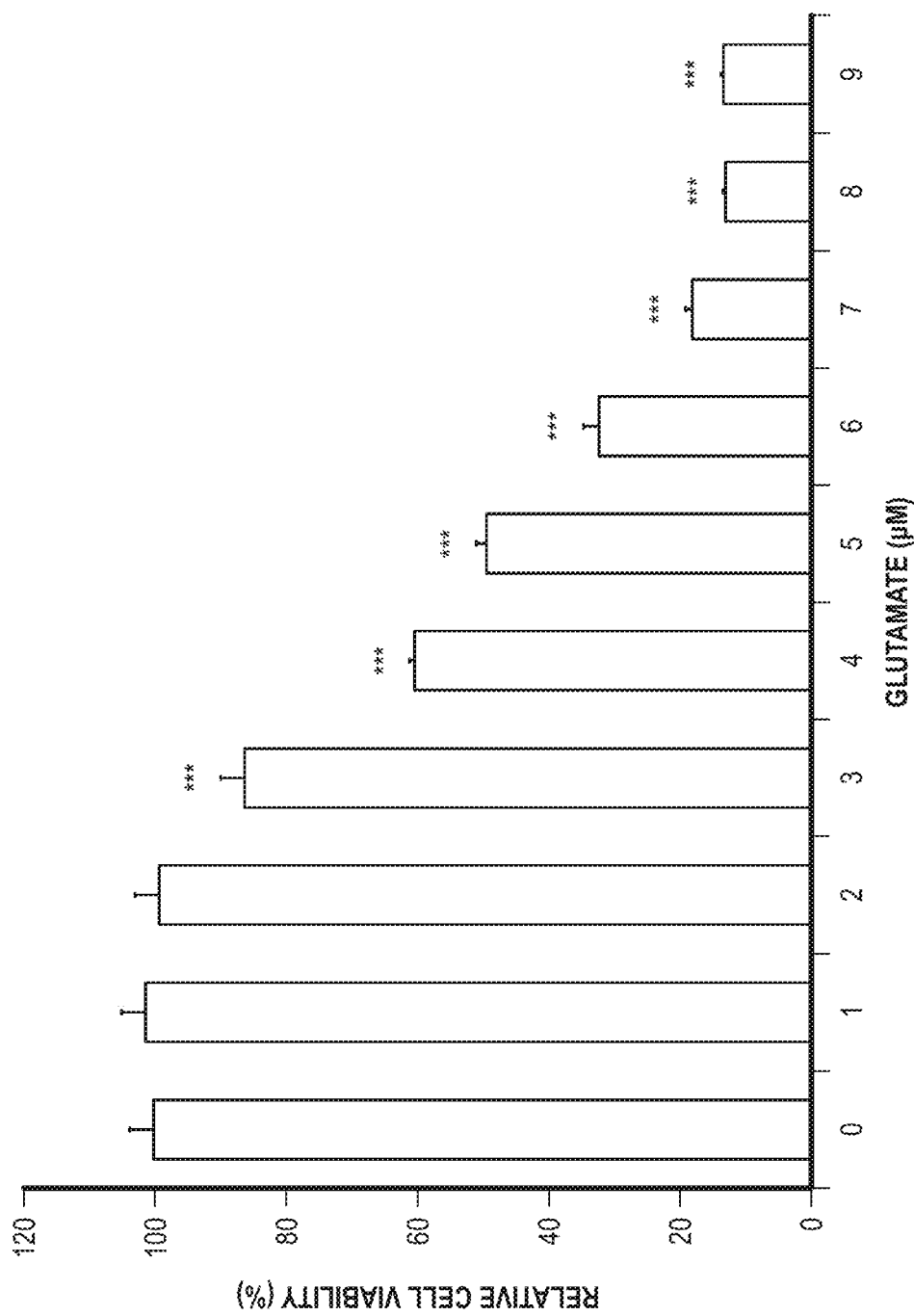
FIG. 4 shows a result of confirming the cytotoxicity of the photoreceptor cells derived from the mouse retina when Compound A is treated in another example of the present disclosure.

After diluting glutamic acid in the cultured cells in the medium and treating the cells with concentrations of 0-9 mM, the cells was incubated for 24 hours, treated with a reagent for cell proliferation analysis (CellTiter96ter AQ$_{ueous}$ One Solution Cell Proliferation Assay Kit) and after 1 hour, the cell viability was measured to compare and analyze the cytotoxicity of glutamic acid to photoreceptor cells derived from the mouse retina. As a result, as shown in FIG. 4, it was found to induce a significant cell viability decrease in a concentration-dependent manner at concentrations of 3 mM or more. The IC$_{50}$ value of glutamic acid was confirmed to be 5.1±0.5 mM.

(2) Cell Protective Effect of Adenosine Derivatives

Figure 5:
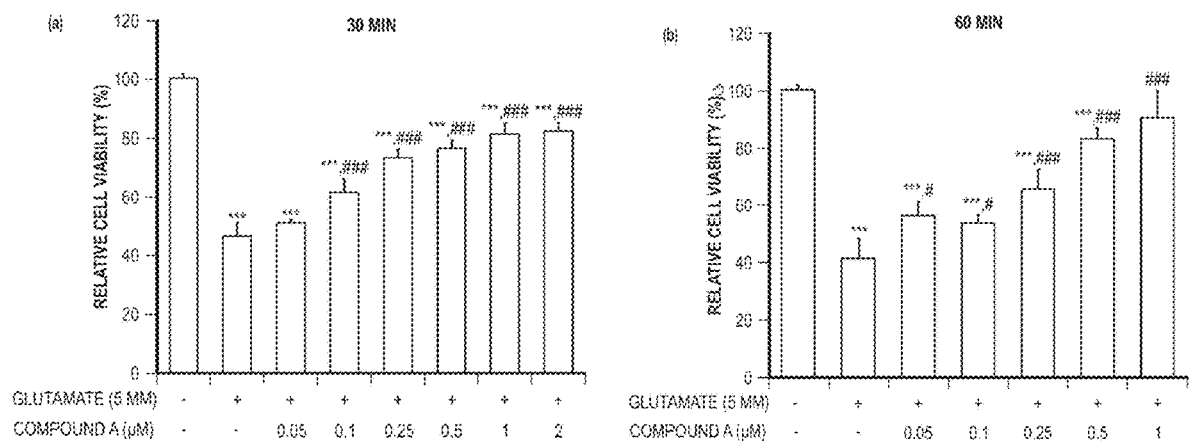
FIG. 5 shows a result of confirming the cell protective effect of Compound A against the cell death induced by glutamic acid in the Example of FIG. 4 ((n=6), (a) pretreatment of Compound A for 30 minutes; (b) pretreatment of Compound A for 1 hour).

As a result of confirming the cell protective effect of Compound A from apoptosis induced by glutamic acid, as shown in FIG. 5 (n=6), it was confirmed that the pretreatment of Compound A inhibits cell viability inhibition by glutamic acid in a concentration-dependent manner up to a concentration of 1 μM. This experimental result means that Compound A has a protective effect against glutamic acid-induced apoptosis. The EC$_{50}$ (50% effective concentration) levels of Compound A were 0.31±0.08 μM and 0.35±0.06 μM for pretreatment for 30 min and 1 hour, respectively, which were similar to each other.

(3) Inhibitory Effect of Adenosine Derivatives on Apoptosis

Figure 6:
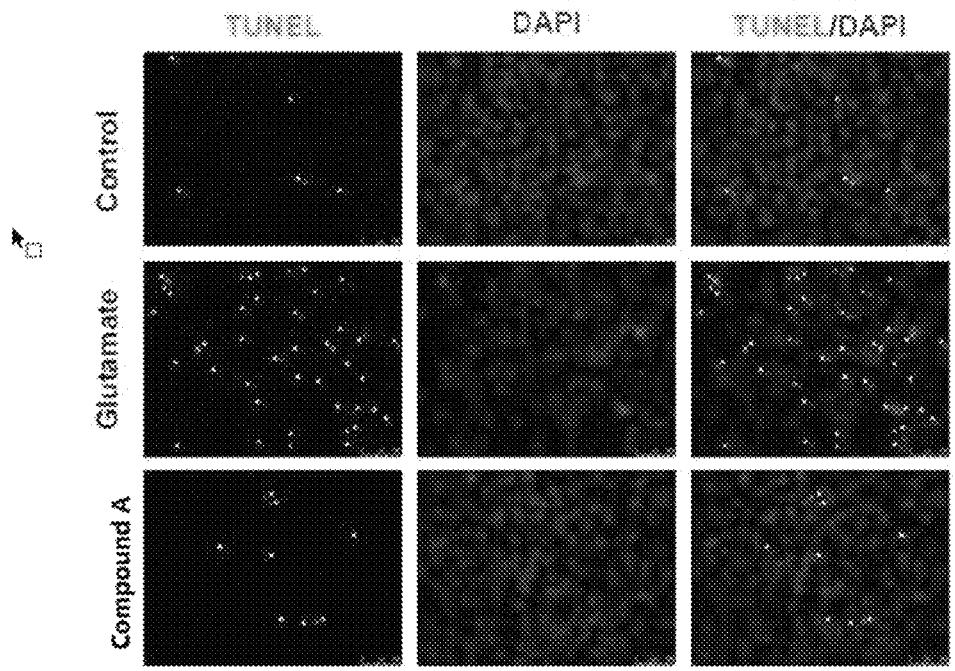
FIG. 6 shows a result of observing the effect of inhibiting the cell death of Compound A in the Example of FIG. 4 by a microscope through TUNEL assay and DAPI staining.

In order to confirm the effect of inducing apoptosis by glutamic acid and inhibiting the effect of Compound A, cells undergoing apoptosis were observed under a microscope through TUNEL assay and DAPI staining. As a result, as shown in FIG. 6, it was confirmed that TUNEL-positive reactions were observed in a large number of nuclei in cells treated with glutamic acid only, but the number was significantly reduced in cells pretreated with Compound A. These results indicate that the Compound A inhibits apoptosis by glutamic acid.

(4) Mitochondrial Protective Effect of Adenosine Derivatives

Figure 7:
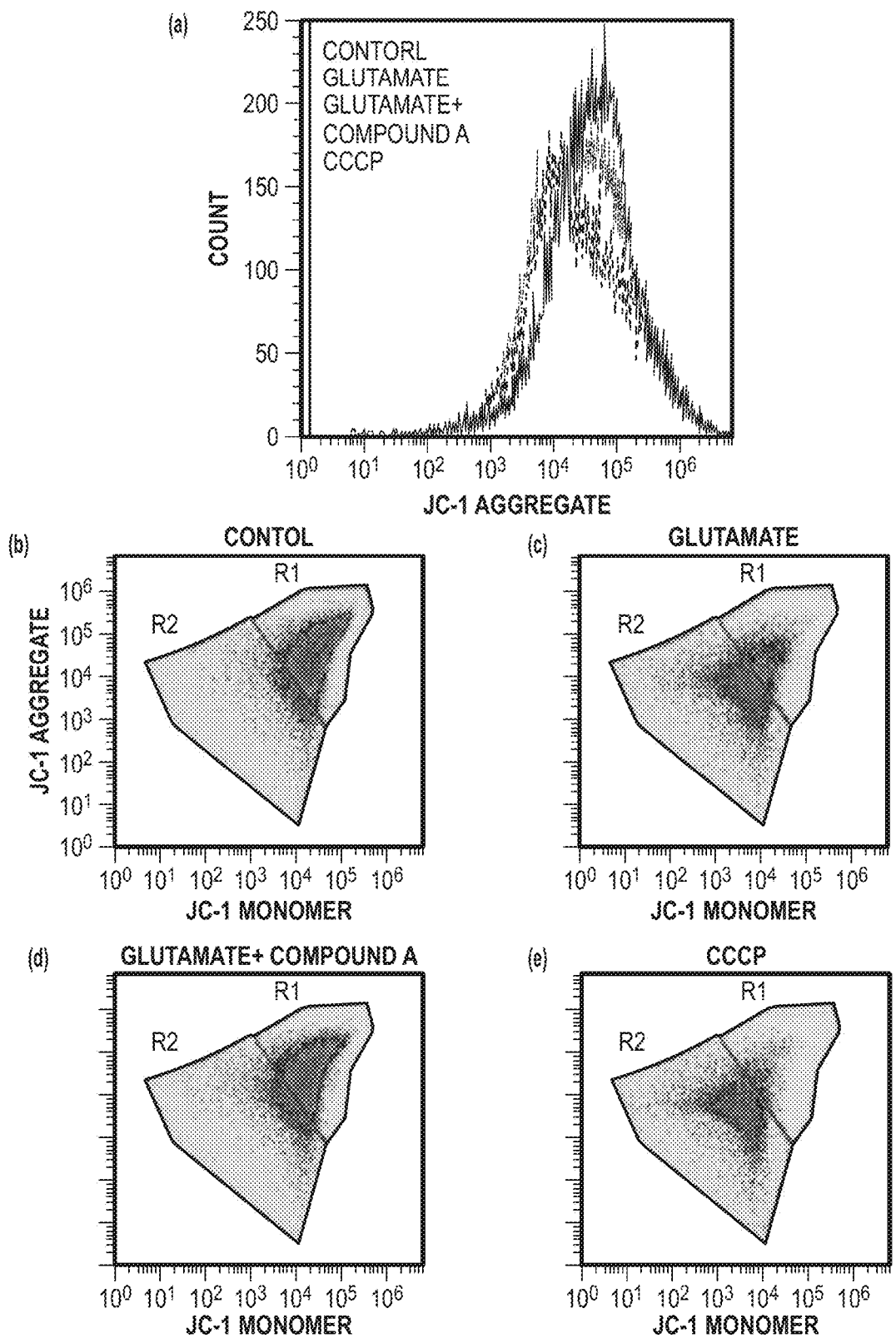
FIG. 7 shows a result of confirming the mitochondrial protective effect of Compound A in the Example of FIG. 4 ((a) JC-1 aggregate, (b) distribution of normal group cells, (c) distribution of experimental group cells treated only with glutamic acid, (d) distribution of experimental group cells treated with glutamic acid after pretreatment with Compound A, (e) distribution of control group cells treated with CCCP only).

Apoptosis by glutamic acid has been reported to be associated with damage to mitochondria. Thus, to confirm what effect Compound A has on mitochondrial damage to glutamic acid, the mitochondrial membrane potential difference was analyzed through a flow cytometer. As a result, as shown in FIG. 7 and Table 4 below, it was confirmed that JC-1 aggregates were decreased in cells treated with glutamic acid only. Similar cell distribution could be confirmed by treatment of CCCP inducing mitochondrial damage. However, in the experimental group pretreated with Compound A, the distribution of cells was found to be similar to that of the normal group. These results indicate that Compound A inhibits the damage of intercellular mitochondria by glutamic acid.

TABLE 4

| | Control | Glutamate | Glutamate + Compound A | CCCP |
|---|---|---|---|---|
| R1 | 86.22 ± 1.12 | 36.13 ± 10.42** | 71.70 ± 1.60** | 9.42 ± 1.48*** |
| R2 | 13.78 ± 1.12 | 63.87 ± 10.42** | 28.30 ± 1.60** | 90.58 ± 1.48*** |

(5) Confirmation of Caspase Activity

Figure 8:
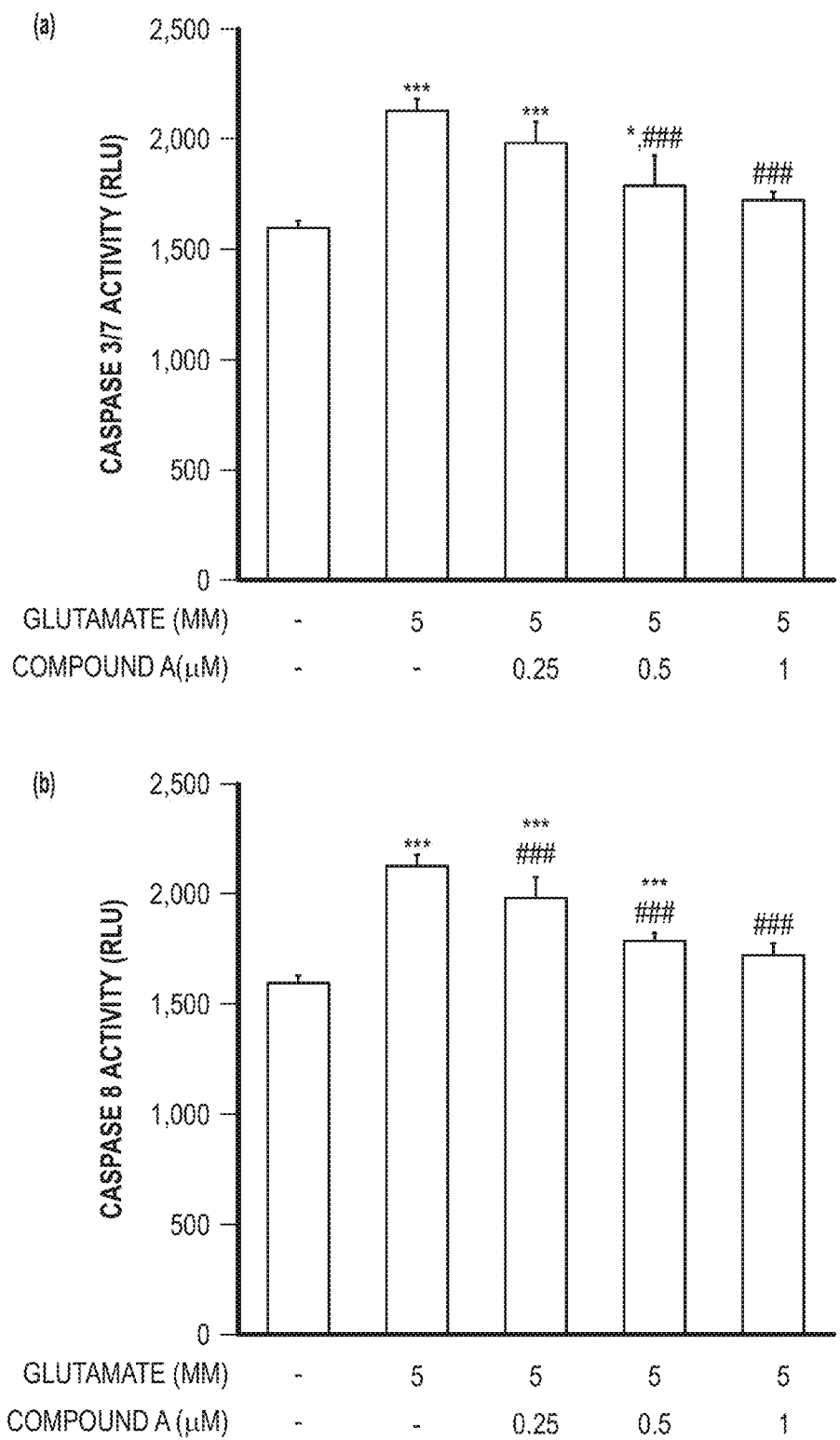
FIG. 8 shows a result of confirming the effect of inhibiting the caspase activity of Compound A in the Example of FIG. 4 ((a) activity of caspase 3/7, (b) activity of caspase 8).

Caspase is known to regulate cell death. Thus, as a result of confirming the action of caspase in cell damage by glutamic acid and the cell protective effect of compound A, as shown in FIG. 8, the activities of caspase 3/7 of cells (FIG. 8(a)) and caspase 8 of cells (FIG. 8(b)) treated with glutamic acid only were significantly increased, and as a result of pretreatment of Compound A, the activity of caspase 3/7 and caspase 8 was inhibited in a concentration-dependent manner. These results indicate that Compound A inhibits cell death by activation of caspase.

(6) Changes in Expression of Apoptosis-Related Proteins

Figure 9:
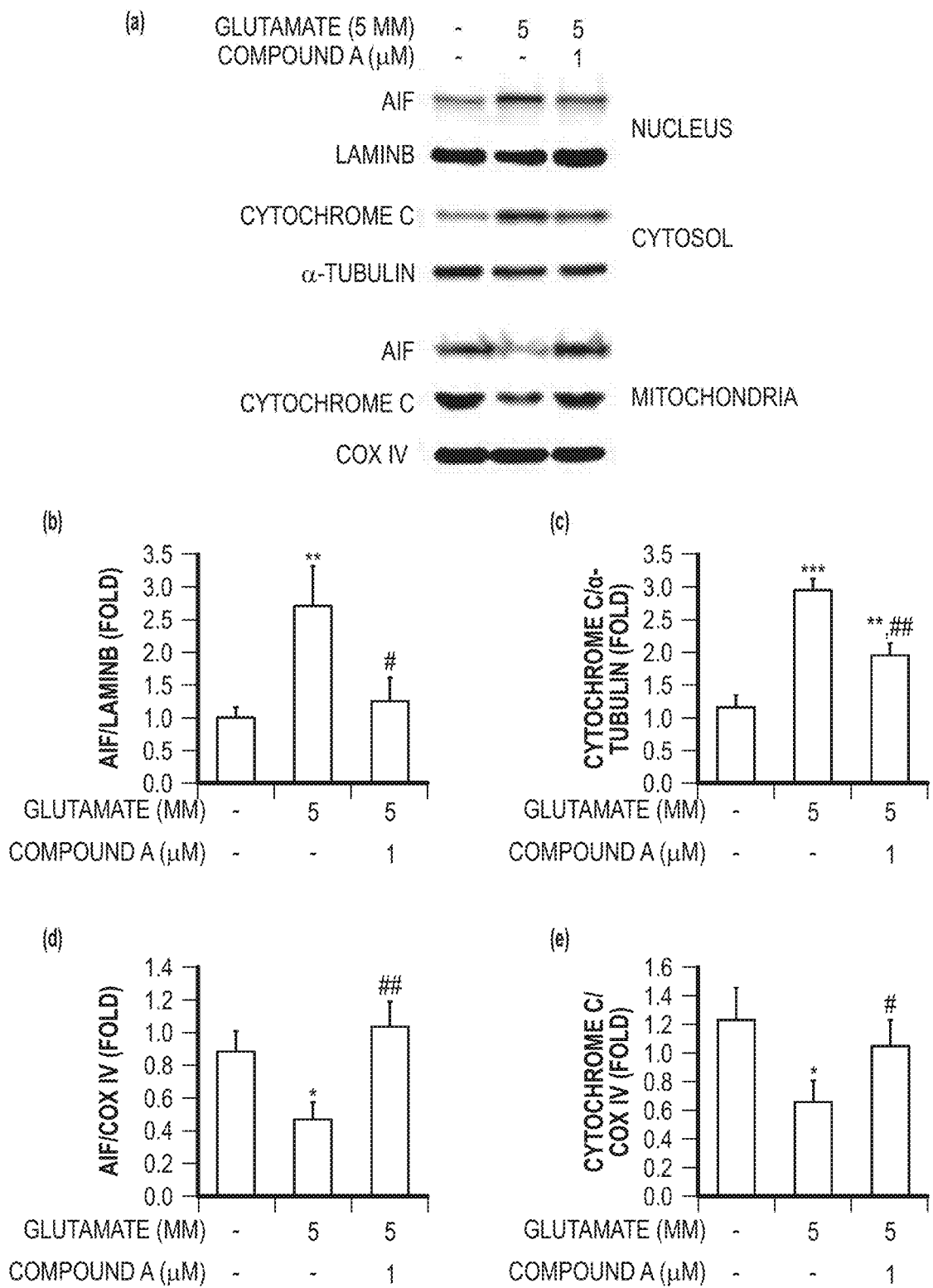
FIG. 9, FIG. 10A, FIG. 10B and FIG. 10C show results of confirming the expression change of the protein related to cell death by Compound A in the Example of FIG. 4 (FIG. 9, (a) protein expression change; (b) AIF protein expression change in the cell nucleus; (c) cytochrome c protein expression change in the cytoplasm; (d) mitochondrial AIF protein expression change; and (e) mitochondrial cytochrome c protein expression change.

In order to confirm the efficacy of Compound A on cell death by glutamic acid, changes in AIF and cytochrome c, which are proteins related to the apoptosis, were analyzed. As a result, as shown in FIG. 9, it was confirmed that in cells treated with glutamic acid only, it was confirmed that AIF and cytochrome c, present in the mitochondria, migrated to the nucleus and cytoplasm, respectively and as a result of pretreatment of Compound A, the expression of AIF and cytochrome c in the nucleus and cytoplasm decreased significantly. Namely, it is confirmed that Compound A significantly inhibits the protein transport change. These results indicate that Compound A inhibits damage to cells by inhibiting damage to mitochondria.

Figure 10A:
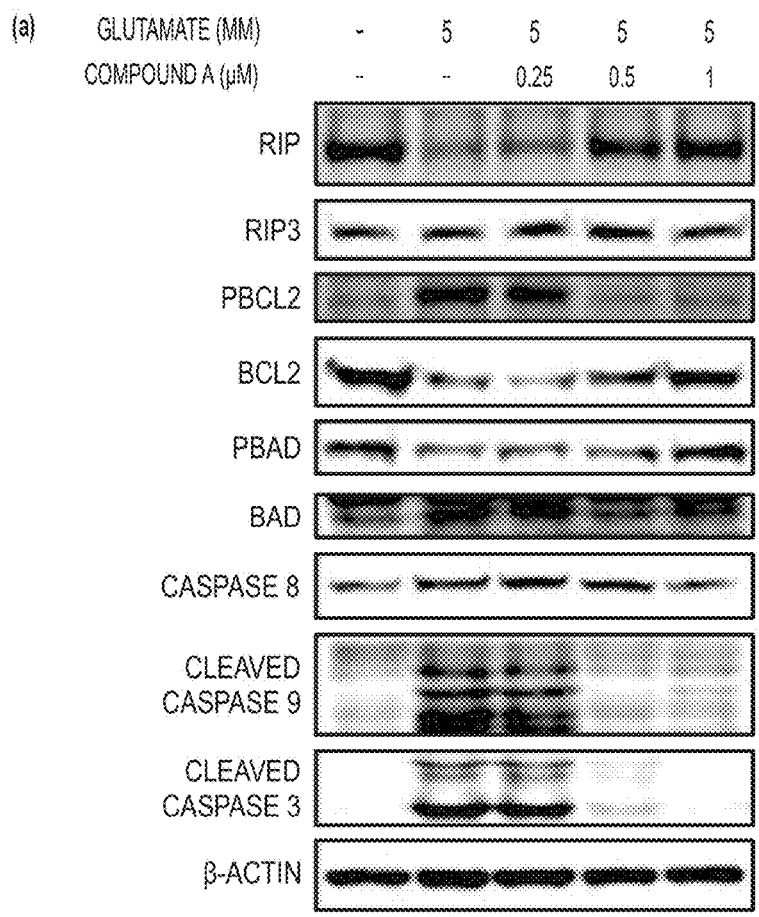
Figure 10A:
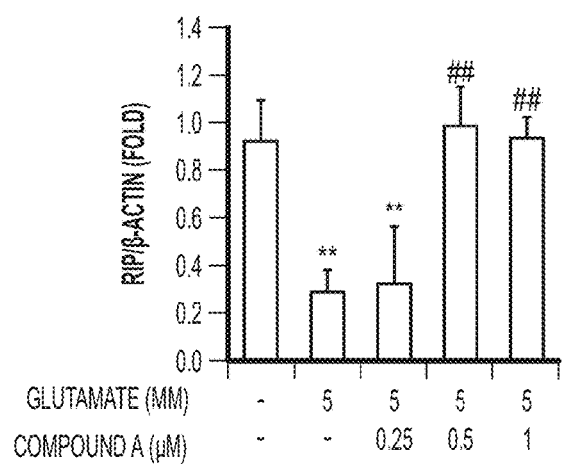
Figure 10A:
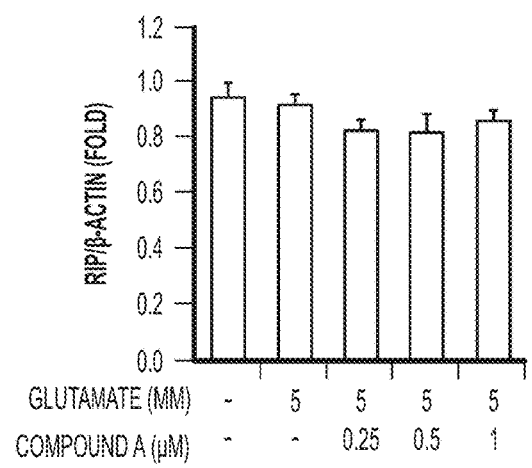
Figure 10B:
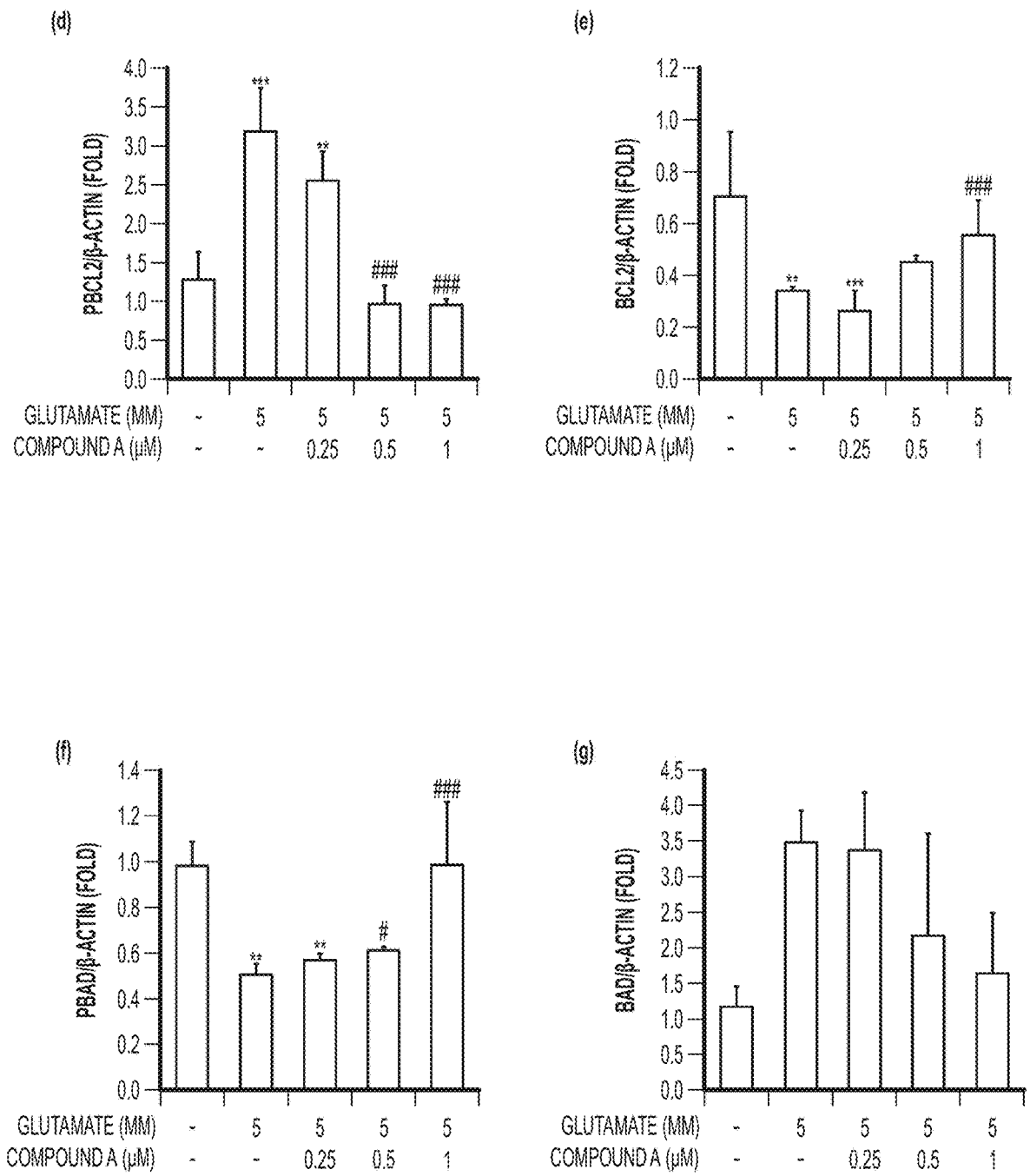
Figure 10C:
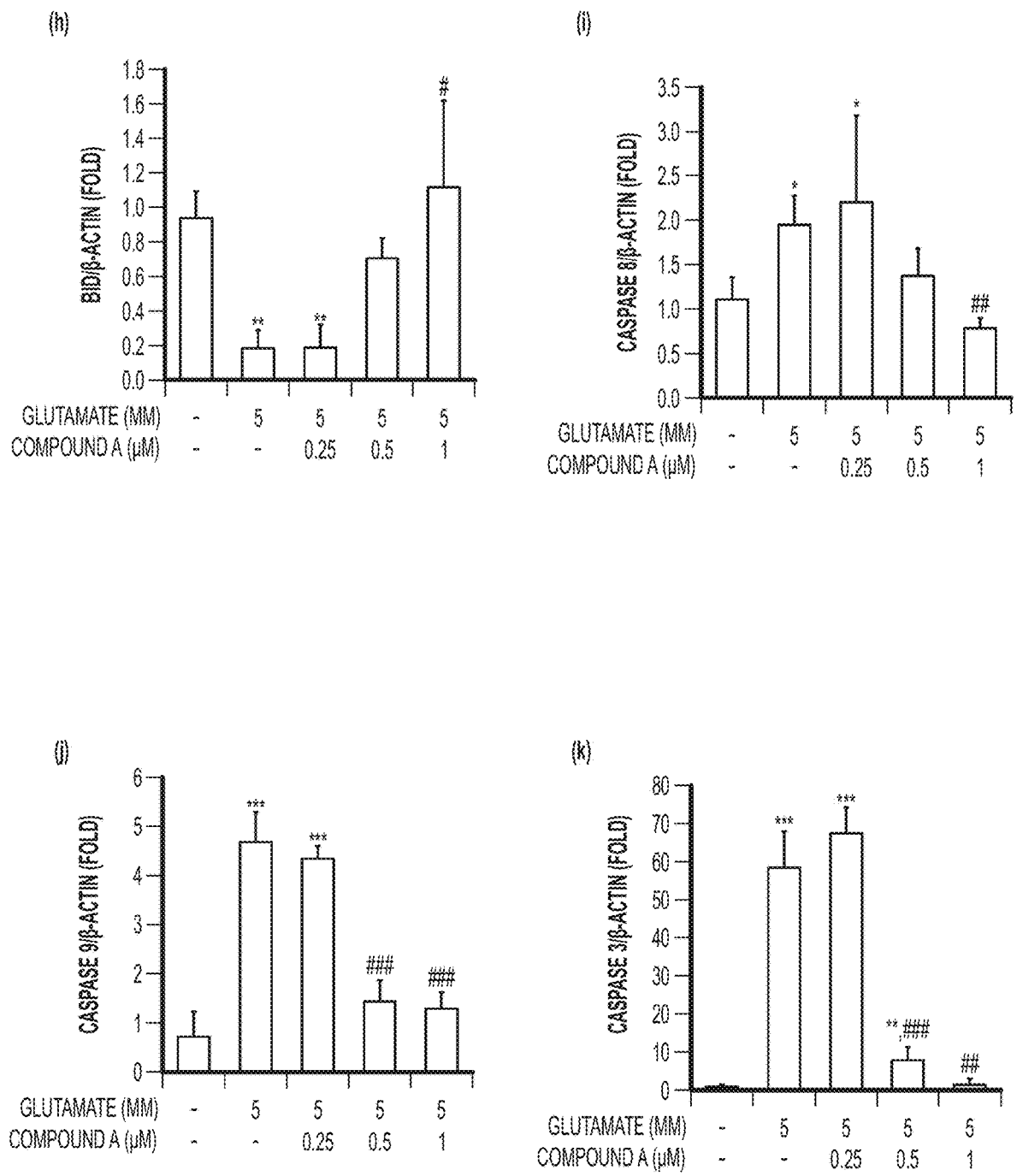

In addition, in order to confirm the mechanism of apoptosis by glutamic acid and the effect of Compound A on it, as a result of analyzing the changes of the apoptosis-related protein, as shown in FIG. 10A to FIG. 10C, it was confirmed that the expression of RIP related to apoptosis was significantly decreased by glutamic acid, but in the experimental group pretreated with Compound A, it was increased again in a concentration-dependent manner. In addition, although the expression of pBcl2, Bcl2, pBad, Bad and BID proteins related to mitochondrial damage was significantly changed by glutamic acid, it was confirmed that the experimental group pretreated with Compound A recovered to the same expression level as the normal group. It was confirmed that caspase 8, cleaved caspase 9 and cleaved caspase 3 were also significantly increased by glutamic acid, but they were significantly decreased in the experimental group pretreated with Compound A. These results indicate that Compound A protects cells by inhibiting apoptosis by glutamic acid.

<Example 3> Experiment of Protective Effect of Eye Drop Containing Adenosine Derivatives on Optic Nerve The following in vivo animal experiments were performed to examine the protective efficacy of the eye drop of the derivatives of the present disclosure for the optic nerve. The eye drop prepared in the Preparation Example 1 was administered into the eyes of 3-month-old normal DAB 2J mice. As a positive control, xalatan, an eye drop used as a therapeutic agent for glaucoma, was administered in the same way, and as a negative control, no treatment was given to the experimental animals.

Figure 11:
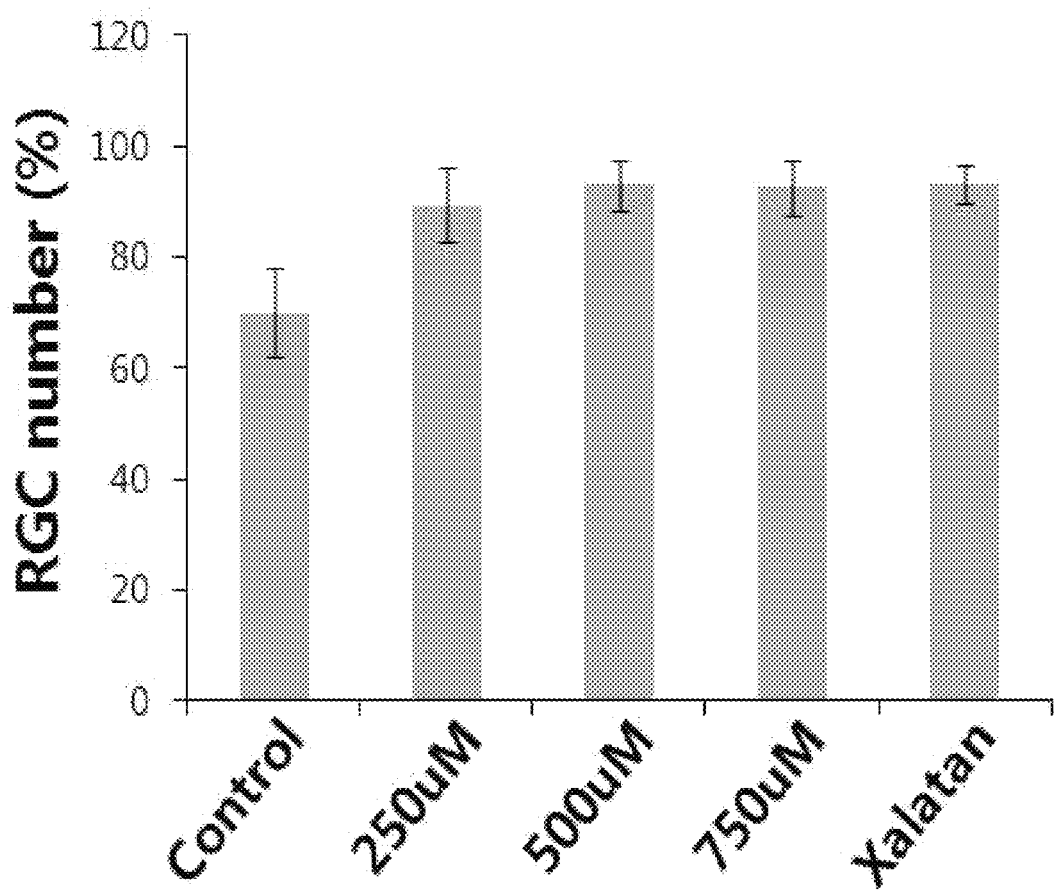
FIG. 11 is a graph showing a result of measuring the number of retinal ganglion cells in the eyeball of a mouse according to another example of the present disclosure.
Figure 12:
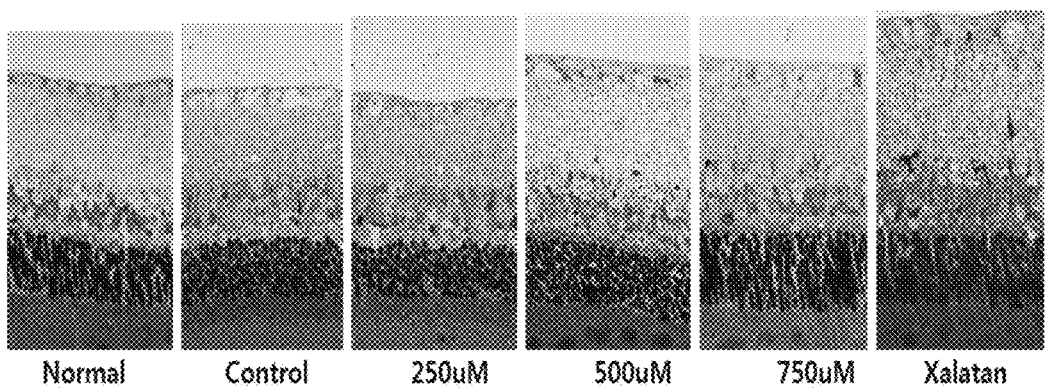
FIG. 12 is a photograph observing histological changes of the mouse retina according to the Embodiment of FIG. 11.

Subsequently, the number of retinal ganglion cells (RGCs) of the experimental animals after 4 months was measured, and the cross-sections were observed, and the results were shown in FIG. 11 and FIG. 12, respectively. In FIG. 11 and FIG. 12, Control represents a negative control, Drug 250, 500 and 750 are eye drops containing the derivative compound (Compound A) at concentrations of 250 µM, 500 µM and 750 µM, respectively, and Xalatan represents a positive control.

Referring to FIG. 11 and FIG. 12, it was confirmed that there was an effect of protecting the optic nerve depending on the dose of the eye drop in mice administered with the eye drop containing the adenosine derivative of the present disclosure.

While the present disclosure has been particularly described with reference to specific embodiments thereof, it is apparent that this specific description is only a preferred embodiment and that the scope of the present disclosure is not limited thereby to those skilled in the art. That is, the practical scope of the present disclosure is defined by the appended claims and their equivalents.

What is claimed is:

1. A method of treating optic nerve disease in a subject comprising:
administering a pharmaceutical composition comprising a compound represented by Chemical Formula 1 or a pharmaceutically acceptable salt thereof as an active ingredient to the subject:

[Chemical Formula 1]

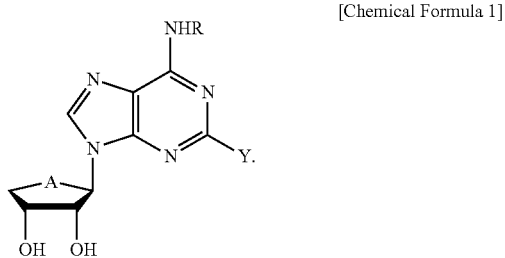

wherein
A is O or S,
R is
a) straight or branched $C_1$ to $C_5$ alkyl unsubstituted, or independently or optionally substituted with 1 or 2 or more $C_6$ to $C_{10}$ aryl,
b) benzyl unsubstituted, or independently or optionally substituted with 1 or 2 or more fluoro, chloro, bromo or straight or branched $C_1$ to $C_4$ alkoxy or
c) benzyl substituted with hydroxycarbonyl, and
Y is H or a halogen element,
wherein the optic nerve disease is selected from the group consisting of ischemic optic neuropathy, traumatic optic neuropathy, and compressive optic neuropathy.

2. The method of treating optic nerve disease of claim 1, wherein the compound represented by the Chemical Formula 1 is a compound represented by Chemical Formula 2:

[Chemical Formula 2]

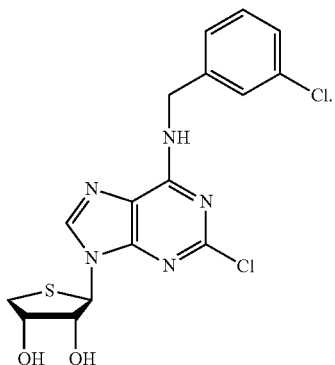

3. The method of treating optic nerve disease of claim 1, wherein the pharmaceutical composition is an oral administration agent.

4. The method of treating optic nerve disease of claim 3, wherein the pharmaceutical composition further comprises at least one excipient selected from the group consisting of methyl cellulose (MC), dimethyl sulfoxide (DMSO), polyethylene glycol (PEG) and distilled water.

5. The method of treating optic nerve disease of claim 4, wherein the excipient comprises 0.5 wt % of methyl cellulose.

6. The method of treating optic nerve disease of claim 3, wherein the compound represented by the Chemical Formula 1 or a pharmaceutically acceptable salt thereof is filled in a capsule in powder form.

7. The method of treating optic nerve disease of claim 3, wherein the compound represented by the Chemical Formula 1 is a compound represented by Chemical Formula 2:

[Chemical Formula 2]

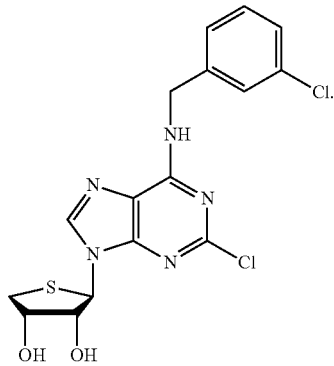

8. The method of treating optic nerve disease of claim 1, wherein the pharmaceutical composition is an eye drop.

* * * * *

SEQUENCE LISTING

```
Sequence total quantity: 11
SEQ ID NO: 1            moltype = DNA  length = 41
FEATURE                 Location/Qualifiers
source                  1..41
                        mol_type = other DNA
                        organism = synthetic construct
SEQUENCE: 1
gctgcgcttt tctcgaatcc gtaaacaagg cttcatgggg g                            41

SEQ ID NO: 2            moltype = DNA  length = 40
FEATURE                 Location/Qualifiers
source                  1..40
                        mol_type = other DNA
                        organism = synthetic construct
SEQUENCE: 2
cgctcatgta cccgctgtat tgtctgccgg actcaaagac                              40

SEQ ID NO: 3            moltype = DNA  length = 40
FEATURE                 Location/Qualifiers
source                  1..40
                        mol_type = other DNA
                        organism = synthetic construct
SEQUENCE: 3
ctccgtagta gccgtggtct gcttcgctgg tagacatcca                              40

SEQ ID NO: 4            moltype = DNA  length = 40
FEATURE                 Location/Qualifiers
source                  1..40
                        mol_type = other DNA
                        organism = synthetic construct
SEQUENCE: 4
tctagaagac tcgggcacct cgtgatcagc tccaggtttg                              40

SEQ ID NO: 5            moltype = DNA  length = 41
FEATURE                 Location/Qualifiers
```

```
source                  1..41
                        mol_type = other DNA
                        organism = synthetic construct
SEQUENCE: 5
aacacgtgga ctctgtcctc cgaagagcac gcaaaccttc c                        41

SEQ ID NO: 6            moltype = DNA  length = 39
FEATURE                 Location/Qualifiers
source                  1..39
                        mol_type = other DNA
                        organism = synthetic construct
SEQUENCE: 6
gacaagcctg tagcccacgt gggggctggg tagagaatg                           39

SEQ ID NO: 7            moltype = DNA  length = 42
FEATURE                 Location/Qualifiers
source                  1..42
                        mol_type = other DNA
                        organism = synthetic construct
SEQUENCE: 7
gccttcttgg gactgatgct tggaaattgg ggtaggaagg ac                       42

SEQ ID NO: 8            moltype = DNA  length = 48
FEATURE                 Location/Qualifiers
source                  1..48
                        mol_type = other DNA
                        organism = synthetic construct
SEQUENCE: 8
gtatcagaac cgcattgcct ccggcttcca gtattgagga gaacagat                 48

SEQ ID NO: 9            moltype = DNA  length = 40
FEATURE                 Location/Qualifiers
source                  1..40
                        mol_type = other DNA
                        organism = synthetic construct
SEQUENCE: 9
cctgtttcct gcctctgaag gtctgctgag acccctcttg                          40

SEQ ID NO: 10           moltype = DNA  length = 40
FEATURE                 Location/Qualifiers
source                  1..40
                        mol_type = other DNA
                        organism = synthetic construct
SEQUENCE: 10
tctagaagac tcgggcacct cgtgatcagc tccaggtttg                          40

SEQ ID NO: 11           moltype = DNA  length = 42
FEATURE                 Location/Qualifiers
source                  1..42
                        mol_type = other DNA
                        organism = synthetic construct
SEQUENCE: 11
gtgccgttga atttgccgtg aatggtgaag gtcggtgtga ac                       42
```